US005216131A

United States Patent [19]

Lasky et al.

[11] Patent Number: 5,216,131

[45] Date of Patent: Jun. 1, 1993

[54] LYMPHOCYTE HOMING RECEPTORS

[75] Inventors: Laurence A. Lasky, Sausalito; Steven D. Rosen, San Francisco; Scott E. Stachel; Mark S. Singer, both of Berkeley; Ted A. Yednock, Fairfax, all of Calif.

[73] Assignee: Genentech, Inc., South San Francisco, Calif.

[21] Appl. No.: 786,149

[22] Filed: Oct. 31, 1991

Related U.S. Application Data

[62] Division of Ser. No. 315,015, Feb. 23, 1989, Pat. No. 5,098,833.

[51] Int. Cl.[5] ........................ C07K 7/10; C07K 13/00

[52] U.S. Cl. .................................. 530/350; 530/300; 530/324

[58] Field of Search ................ 530/300, 324, 350, 387

[56] References Cited

U.S. PATENT DOCUMENTS 5,002,873 3/1991 St. John et al. .................... 435/69.1

OTHER PUBLICATIONS

Yednock et al., J. Cell Biology 104:725-731 (1987).
Woodruff et al., Ann. Rev. Immunol. 5:201-222 (1987).
Chin et al., J. Immunol. 136:2556-2561 (1986).
Butcher, E.C., Current Topics in Microbiol. and Immunol. 128: Springer-Verlag Berlin-Heidelberg, pp. 85-122 (1986).
Gallatin et al., Cell 44:673-680 (1986).
Glabe et al., J. Cell Biol. 94:123-128 (1982).
Mountz et al., J. Immunol. 140(9):2943-2949.
Rosen et al., J. Immunol. 140(6):1895-1902 (1989).
Jalkanen et al., Eur. J. Immunol. 16:1195-1202 (1986).
Jalkanen et al., J. Cell Biology 105:983-990 (1987).
Stoolman et al., J. Cell Biology 99:1535-1540 (1984).
Bischoff, R., J. Cell Biology 102:2273-2280 (1986).
Bleil & Wassarman, Proc. Natl. Acad. Sci. U.S.A. 85:6778-6782 (1988).
Brandley et al., J. Cell Biology 105:991-997 (1987).
Crocker & Gordon, J. Exp. Med. 164:1862-1875 (1986).
DeAngelis & Glabe, J. Biol. Chem. 262(29):13946-13952 (1987).
Duijvestijn & Hamann, Immunology Today 10(1):23-28 (1989).
Jalkanen et al., Ann. Rev. Med. 38:467-476 (1987).
Stoolman et al., Blood 70(6):1842-1850 (1987).
Grabel et al., Cell 17:477-484 (1979).
Jalkanen & Butcher, Blood 66:577-582 (1985).
Knapp et al., Immunology Today 10(8):253-258 (1989).
Kunemund et al., J. Cell Biology 106:213-223 (1988).
Lopez et al., J. Cell. Biology 101:1501-1510 (1985).
Rasmussen et al., J. Immunology 135(1):19-24 (1985).
Rosen et al., Science 228:1005-1007 (1985).
Paulson, J. C., The Receptors 2:131-219 (1985).
Siegelman et al., Science 243:1165-1172 (1989).
St. John et al., Science, 231:845-850.
Lewinsohn, et al., J. Immunol. 138:4313-4321.
Bowen et al., J. Cell Biol. 110:147-153 (1990).
Schrader, J., Academic Press, Inc., 375-391 (1988).
Hershko, A., J. Biol. Chem. 263:15237-15240 (1988).
Young et al., Science, 222:778-782 (1983).
Jacobs et al., Nature 313:806810 (1985).

*Primary Examiner*—Robert J. Hill, Jr.
*Assistant Examiner*—John D. Ulm
*Attorney, Agent, or Firm*—Ginger R. Dreger

[57] ABSTRACT

DNA isolates coding for the lymphocyte homing receptor and methods of obtaining such DNA are provided, together with expression systems for recombinant production of the lymphocyte homing receptor useful in therapeutic or diagnostic compositions.

16 Claims, 15 Drawing Sheets

```
GAATTCCAGTGTGCTGGCTTCCTCACCTGCAGCACAGCACACTCCTTTGGGCAAGGACCTGAGACCCTTGTGCTAAGTC

                                                   1
                                                  MET ILE PHE PRO TRP LYS CYS
AAGAGGCTCAATGGGCTGCAGAAGAACTAGAGAAGGACCAAGCAAAGCC  ATG ATA TTT CCA TGG AAA TGT

        10                                         20          SIGNAL SEQUENCE
GLN SER THR GLN ARG ASP LEU TRP ASN ILE PHE LYS LEU TRP GLY TRP THR MET LEU CYS
CAG AGC ACC CAG AGG GAC TTA TGG AAC ATC TTC AAG TTG TGG GGG TGG ACA ATG CTC TGT

        30                                   PROBABLE N-TERMINUS
CYS ASP PHE LEU ALA HIS HIS GLY THR TYR CYS TRP THR TYR HIS TYR SER GLU LYS PRO
TGT GAT TTC CTG GCA CAT CAT GGA ACC TAC TGC TGG ACT TAC CAT TAT TCT GAA AAA CCC

        50                                      60
MET ASN TRP GLN ARG ALA ARG ARG PHE CYS ARG ASP ASN TYR THR ASP LEU VAL ALA ILE
ATG AAC TGG CAA AGG GCT AGA AGA TTC TGC CGA GAC AAT TAC ACA GAT TTA GTT GCC ATA

        70                                      80
GLN ASN LYS ALA GLU ILE GLU TYR LEU GLU LYS THR LEU PRO PHE SER ARG SER TYR TYR
CAA AAC AAG GCG GAA ATT GAG TAT CTG GAG AAG ACT CTG CCC TTC AGT CGT TCT TAC TAC

        90                                      100
TRP ILE GLY ILE ARG LYS ILE GLY GLY ILE TRP THR TRP VAL GLY THR ASN LYS SER LEU
TGG ATA GGA ATC CGG AAG ATA GGA GGA ATA TGG ACG TGG GTG GGA ACC AAC AAA TCT CTC

        110                                     120
THR GLU GLU ALA GLU ASN TRP GLY ASP GLY GLU PRO ASN ASN LYS LYS ASN LYS GLU ASP
ACT GAA GAA GCA GAG AAC TGG GGA GAT GGT GAG CCC AAC AAC AAG AAG AAC AAG GAG GAC

        130                                     140
CYS VAL GLU ILE TYR ILE LYS ARG ASN LYS ASP ALA GLY LYS TRP ASN ASP ASP ALA CYS
TGC GTG GAG ATC TAT ATC AAG AGA AAC AAA GAT GCA GGC AAA TGG AAC GAT GAC GCC TGC

        150                                     160
HIS LYS LEU LYS ALA ALA LEU CYS TYR THR ALA SER CYS GLN PRO TRP SER CYS SER GLY
CAC AAA CTA AAG GCA GCC CTC TGT TAC ACA GCT TCT TGC CAG CCC TGG TCA TGC AGT GGC
```

FIG. 1-1

GAATTCCAGTGTGCTGGCTTCCTCACCTGCAGCACAGCACACTCCTTTGGGCAAGGACCTGAGACCCTTGTGCTAAGTC

1
MET ILE PHE PRO TRP LYS CYS
AAGAGGCTCAATGGGCTGCAGAAGAACTAGAGAAGGACCAAGCAAAGCC ATG ATA TTT CCA TGG AAA TGT 10 20 *SIGNAL SEQUENCE*
GLN SER THR GLN ARG ASP LEU TRP ASN ILE PHE LYS LEU TRP GLY TRP THR MET LEU CYS
CAG AGC ACC CAG AGG GAC TTA TGG AAC ATC TTC AAG TTG TGG GGG TGG ACA ATG CTC TGT

30 *PROBABLE N-TERMINUS*
CYS ASP PHE LEU ALA HIS HIS GLY THR TYR CYS TRP THR TYR HIS TYR SER GLU LYS PRO
TGT GAT TTC CTG GCA CAT CAT GGA ACC TAC TGC TGG ACT TAC CAT TAT TCT GAA AAA CCC 50 60
MET ASN TRP GLN ARG ALA ARG ARG PHE CYS ARG ASP ASN TYR THR ASP LEU VAL ALA ILE
ATG AAC TGG CAA AGG GCT AGA AGA TTC TGC CGA GAC AAT TAC ACA GAT TTA GTT GCC ATA 70 80
GLN ASN LYS ALA GLU ILE GLU TYR LEU GLU LYS THR LEU PRO PHE SER ARG SER TYR TYR
CAA AAC AAG GCG GAA ATT GAG TAT CTG GAG AAG ACT CTG CCC TTC AGT CGT TCT TAC TAC 90 100
TRP ILE GLY ILE ARG LYS ILE GLY GLY ILE TRP THR TRP VAL GLY THR ASN LYS SER LEU
TGG ATA GGA ATC CGG AAG ATA GGA GGA ATA TGG ACG TGG GTG GGA ACC AAC AAA TCT CTC 110 120
THR GLU GLU ALA GLU ASN TRP GLY ASP GLY GLU PRO ASN ASN LYS LYS ASN LYS GLU ASP
ACT GAA GAA GCA GAG AAC TGG GGA GAT GGT GAG CCC AAC AAC AAG AAG AAC AAG GAG GAC 130 140
CYS VAL GLU ILE TYR ILE LYS ARG ASN LYS ASP ALA GLY LYS TRP ASN ASP ASP ALA CYS
TGC GTG GAG ATC TAT ATC AAG AGA AAC AAA GAT GCA GGC AAA TGG AAC GAT GAC GCC TGC 150 160
HIS LYS LEU LYS ALA ALA LEU CYS TYR THR ALA SER CYS GLN PRO TRP SER CYS SER GLY
CAC AAA CTA AAG GCA GCC CTC TGT TAC ACA GCT TCT TGC CAG CCC TGG TCA TGC AGT GGC

FIG. 1-2

```
            170                                                180
HIS GLY GLU CYS VAL GLU ILE ILE ASN ASN HIS THR CYS ASN CYS ASP VAL GLY TYR TYR
CAT GGA GAA TGT GTA GAA ATC ATC AAT AAT CAC ACC TGC AAC TGT GAT GTG GGG TAC TAT

            190                                                200
GLY PRO GLN CYS GLN LEU VAL ILE GLN CYS GLU PRO LEU GLU ALA PRO GLU LEU GLY THR
GGG CCC CAG TGT CAG CTT GTG ATT CAG TGT GAG CCT TTG GAG GCC CCA GAG CTG GGT ACC

            210                                                220
MET ASP CYS THR HIS PRO PHE GLY ASN PHE SER PHE SER SER GLN CYS ALA PHE SER CYS
ATG GAC TGT ACT CAC CCC TTT GGA AAC TTC AGC TTC AGC TCA CAG TGT GCC TTC AGC TGC

            230                                                240
SER GLU GLY THR ASN LEU THR GLY ILE GLU GLU THR THR CYS GLY PRO PHE GLY ASN TRP
TCT GAA GGA ACA AAC TTA ACT GGG ATT GAA GAA ACC ACC TGT GGA CCA TTT GGA AAC TGG

            250                                                260
SER SER PRO GLU PRO THR CYS GLN VAL ILE GLN CYS GLU PRO LEU SER ALA PRO ASP LEU
TCA TCT CCA GAA CCA ACC TGT CAA GTG ATT CAG TGT GAG CCT CTA TCA GCA CCA GAT TTG

            270                                                280
GLY ILE MET ASN CYS SER HIS PRO LEU ALA SER PHE SER PHE THR SER ALA CYS THR PHE
GGG ATC ATG AAC TGT AGC CAT CCC CTG GCC AGC TTC AGC TTT ACC TCT GCA TGT ACC TTC

            290                                                300
ILE CYS SER GLU GLY THR GLU LEU ILE GLY LYS LYS LYS THR ILE CYS GLU SER SER GLY
ATC TGC TCA GAA GGA ACT GAG TTA ATT GGG AAG AAG AAA ACC ATT TGT GAA TCA TCT GGA

            310                                                320
ILE TRP SER ASN PRO SER PRO ILE CYS GLN LYS LEU ASP LYS SER PHE SER MET ILE LYS
ATC TGG TCA AAT CCT AGT CCA ATA TGT CAA AAA TTG GAC AAA AGT TTC TCA ATG ATT AAG

            330                                                340   STOP TRANSFER SEQUENCE
GLU GLY ASP TYR ASN PRO LEU PHE ILE PRO VAL ALA VAL MET VAL THR ALA PHE SER GLY
GAG GGT GAT TAT AAC CCC CTC TTC ATT CCA GTG GCA GTC ATG GTT ACT GCA TTC TCT GGG
                    ●●●●●●●●●●●●●●●●●●●●●●●●●●●●●●●●●●●●●●●●●●●●●●●●●●●●●●●●●●●
```

FIG. 1-3

```
        350                                    360
LEU ALA PHE ILE ILE TRP LEU ALA ARG ARG LEU LYS LYS GLY LYS LYS SER LYS ARG SER
TTG GCA TTT ATC ATT TGG CTG GCA AGG AGA TTA AAA AAA GGC AAG AAA TCC AAG AGA AGT
●●●●●●●●●●●●●●●●●●●●●●●●●●●●●●●●●

        370     372
MET ASN ASP PRO TYR OC
ATG AAT GAC CCA TAT TAA ATCGCCCTTGGTGAAAGAAAATTCTTGGAATACTAAAAATCATGAGATCCTTTA

AATCCTTCCATGAAACGTTTTGTGTGGTGGCACCTCCTACGTCAAACATGAAGTGTGTTCCTTCAGTGCATCTGGGAA

GATTTCTACCCGACCAACAGTTCCTTCAGCTTCCATTTCGCCCCTCATTTATCCCTCAACCCCCAGCCCACAGGTGTT

TATACAGCTCAGCTTTTTGTCTTTTCTGAGGAGAAACAAATAAGACCATAAGGGAAAGGATTCATGTGGAATATAAAG

ATGGCTGACTTTGCTCTTTCTTGACTCTTGTTTTCAGTTTCAATTCAGTGCTGTACTTGATGACAGACACTTCTAAAT

GAAGTGCAAATTTGATACATATGTGAATATGGACTCAGTTTTCTTGCAGATCAAATTTCACGTCGTCTTCTGTATACT

GTGGAGGTACACTCTTATAGAAAGTTCAAAAAGTCTACGCTCTCCTTTCTTTCTAACTCCAGTGAAGTAATGGGGTCC

TGCTCAAGTTGAAAGAGTCCTATTTGCACTGTAGCCTCGCCGTCTGTGAATTGGACCATCCTATTTAACTGGCTTCAG

GCCTCCCCACCTTCTTCAGCCACCTCTCTTTTTCAGTTGGCTGACTTCCACACCTAGCATCTCATGAGTGCCAAGCAA

AAGGAGAGAAGAGAGAAATAGCCTGCGCGGTTTTTTAGTTTGGGGGTTTTGCTGTTTCCTTTTATGAGACCCATTCCT

ATTTCTTATAGTCAATGTTTCTTTTATCACGATATTATTAGTAAGAAAACATCACTGAAATGCTAGCTGCAAGTGACA

TCTCTTTGATGTCATATGGAAGAGTTAAAACAGGTGGAGAAATTCCTTGATTCACAATGAAATGCTCTCCTTTCCCCT

GCCCCCAGAACTTTTATCCACTTACCTAGATTCTACATATTCTTTAAATTTCATCTCAGGCCTCCCTCAACCCCACGG

GGCCGCCAGCACACTGGAATTC
```

FIG.2-1

```
GAATTCTCGAGCTCGTCGACCACGCCCTCCTTGTGCAAGAACTCTGAGCCCCAGGTGCAGGAGGCTGAGGCCTGCAGAG

                             1                             10
                            MET VAL PHE PRO TRP ARG CYS GLU GLY THR TYR TRP GLY
AGACTTGCAGAGAGACCCAGCAAGCC  ATG GTG TTT CCA TGG AGA TGT GAG GGT ACT TAC TGG GGC

                         20         SIGNAL SEQUENCE         30
SER ARG ASN ILE LEU LYS LEU TRP VAL TRP THR LEU LEU CYS CYS ASP PHE LEU ILE HIS
TCG AGG AAC ATC CTG AAG CTG TGG GTC TGG ACA CTG CTC TGT TGT GAC TTC CTG ATA CAC

        N-TERMINUS ↓     40                 ••••••••••••••••••••50••••••••••••
HIS GLY THR HIS CYS TRP THR TYR HIS TYR SER GLU LYS PRO MET ASN TRP GLU ASN ALA
CAT GGA ACT CAC TGT TGG ACT TAC CAT TAT TCT GAA AAG CCC ATG AAC TGG GAA AAT GCT

                         60                                 70
ARG LYS PHE CYS LYS GLN ASN TYR THR ASP LEU VAL ALA ILE GLN ASN LYS ARG GLU ILE
AGA AAG TTC TGC AAG CAA AAT TAC ACA GAT TTA GTC GCC ATA CAA AAC AAG AGA GAA ATT

                         80                                 90
GLU TYR LEU GLU ASN THR LEU PRO LYS SER PRO TYR TYR TYR TRP ILE GLY ILE ARG LYS
GAG TAT TTA GAG AAT ACA TTG CCC AAA AGC CCT TAT TAC TAC TGG ATA GGA ATC AGG AAA

                         100                                110
ILE GLY LYS MET TRP THR TRP VAL GLY THR ASN LYS THR LEU THR LYS GLU ALA GLU ASN
ATT GGG AAA ATG TGG ACA TGG GTG GGA ACC AAC AAA ACT CTC ACT AAA GAA GCA GAG AAC

                         120                                130
TRP GLY ALA GLY GLU PRO ASN ASN LYS LYS SER LYS GLU ASP CYS VAL GLU ILE TYR ILE
TGG GGT GCT GGG GAG CCC AAC AAC AAG AAG TCC AAG GAG GAC TGT GTG GAG ATC TAT ATC

                         140                                150
LYS ARG GLU ARG ASP SER GLY LYS TRP ASN ASP ASP ALA CYS HIS LYS ARG LYS ALA ALA
AAG AGG GAA CGA GAC TCT GGG AAA TGG AAC GAT GAC GCC TGT CAC AAA CGA AAG GCA GCT
```

FIG.2-2

```
                          160                                     170
LEU CYS TYR THR ALA SER CYS GLN PRO GLY SER CYS ASN GLY ARG GLY GLU CYS VAL GLU
CTC TGC TAC ACA GCC TCT TGC CAG CCA GGG TCT TGC AAT GGC CGT GGA GAA TGT GTG GAA

                          180                                     190
THR ILE ASN ASN HIS THR CYS ILE CYS ASP ALA GLY TYR TYR GLY PRO GLN CYS GLN TYR
ACT ATC AAC AAT CAC ACG TGC ATC TGT GAT GCA GGG TAT TAC GGG CCC CAG TGT CAG TAT

                          200                                     210
VAL VAL GLN CYS GLU PRO LEU GLU ALA PRO GLU LEU GLY THR MET ASP CYS ILE HIS PRO
GTG GTC CAG TGT GAG CCT TTG GAG GCC CCT GAG TTG GGT ACC ATG GAC TGC ATC CAC CCC

                          220                                     230
LEU GLY ASN PHE SER PHE GLN SER LYS CYS ALA PHE ASN CYS SER GLU GLY ARG GLU LEU
TTG GGA AAC TTC AGC TTC CAG TCC AAG TGT GCT TTC AAC TGT TCT GAG GGA AGA GAG CTA

                          240                                     250
LEU GLY THR ALA GLU THR GLN CYS GLY ALA SER GLY ASN TRP SER SER PRO GLU PRO ILE
CTT GGG ACT GCA GAA ACA CAG TGT GGA GCA TCT GGA AAC TGG TCA TCT CCA GAG CCA ATC

                          260                                     270
CYS GLN VAL VAL GLN CYS GLU PRO LEU GLU ALA PRO GLU LEU GLY THR MET ASP CYS ILE
TGC CAA GTG GTC CAG TGT GAG CCT TTG GAG GCC CCT GAG TTG GGT ACC ATG GAC TGC ATC

                          280                                     290
HIS PRO LEU GLY ASN PHE SER PHE GLN SER LYS CYS ALA PHE ASN CYS SER GLU GLY ARG
CAC CCC TTG GGA AAC TTC AGC TTC CAG TCC AAG TGT GCT TTC AAC TGT TCT GAG GGA AGA

                          300                                     310
GLU LEU LEU GLY THR ALA GLU THR GLN CYS GLY ALA SER GLY ASN TRP SER SER PRO GLU
GAG CTA CTT GGG ACT GCA GAA ACA CAG TGT GGA GCA TCT GGA AAC TGG TCA TCT CCA GAG

                          320                                     330
PRO ILE CYS GLN GLU THR ASN ARG SER PHE SER LYS ILE LYS GLU GLY ASP TYR ASN PRO
CCA ATC TGC CAA GAG ACA AAC AGA AGT TTC TCA AAG ATC AAA GAA GGT GAC TAC AAC CCC
```

```
                              340     STOP TRANSFER SEQUENCE                 350
LEU PHE ILE PRO VAL ALA VAL MET VAL THR ALA PHE SER GLY LEU ALA PHE LEU ILE TRP
CTC TTC ATT CCT GTA GCC GTC ATG GTC ACC GCA TTC TCG GGG CTG GCA TTT CTC ATT TGG

                              360                                    370     372
LEU ALA ARG ARG LEU LYS LYS GLY LYS LYS SER GLN GLU ARG MET ASP ASP PRO TYR OP
CTG GCA AGG CGG TTA AAA AAA GGC AAG AAA TCT CAA GAA AGG ATG GAT GAT CCA TAC TGA

TTCATCCTTTGTGAAAGGAAAGCCATGAAGTGCTAAAGACAAAACATTGGAAAATAACGTCAAGTCCTCCCGTGAAGA

TTTTACACGCAGGCATCTCCCACATTAGAGATGCAGTGTTTGCTCAACGAATCTGGAAGGATTTCTTCATGACCAACA

GCTCCTCCTAATTTCCCCTCGCTCATTCATCCCATTAACCCTATCCCATAATGTGTGTCTATACAGAGTAGTATTTTA

TCATCTTTTCTGTGGAGGAACAAGCAAAAGTGTTACTGTAGAATATAAAGACAGCTGCTTTTACTCTTTCCTAACTCT

TGTTTCCTAGTTCAATTCAGCACAGAAGCTAATGCCAAACACAGTGAAAATATGATCCATGAGTAATTGGAAACTCAG

ACTCCTTGCGCATAGTACGTACCCTATGTAACATCGACAAAAATCTTTCATTTCCACCTCCAAAGAACAGTGCTCTAT

TCAAGTTGGGAAAGTCCTACTTCCTCTGTAGACCCACTATCTGTGAGTGACAGCCACTGTAGCTGTTCACATTAACCT

TCCCCATCTCCTTTTCCTAGGAGAATAATTCCACACACTGCACCCCATGATGGCCACCAAACATCAAAGAAGGGAAAA

TCTCCTGCATTGAGTTTTAGTTTTGAGTTTTCCCTTCTCTTTATTAGATCTCTGATGGTTCCTTGAAGTCAGTGTTCT

GATGATTATTAATAGTTAATGATAACACAACCCACTCTCTTGGAGCTGATGTTATGAAGACAACAGGTAGAAAAATTC

CTGGGCTCAGGCTGGAGTGACACCCTTTTCTTTCCCTAACATCTTCTACTCAGATACCTAAATTTAAGATTCAGGACA

GCTGTCCCCAACTCTTACCATGTCTTTTATAACTTGCTCCTTAACTTGCCCAACCTGTAGGCTATCTCATTTTCTCGC

TTCACTCTGCAAGGTTTATAACATGATGAATTTAAATACAAAAAAAAAAAAAA
```

FIG.2-3

COMPLEMENT BINDING REPEAT 1 mHR E A P E L G T M D C I H P L G N F S F Q S K C A F N C S E G R E L L G T A E T Q C G A S G N W S S P
hHR E A P E L G T M D C T H P F G N F S F S S Q C A F S C S E G T N L T G I E T T C G P F G N W S S P

COMPLEMENT BINDING REPEAT 2 mHR E P I C Q V Q C E P L E A P E L G T M D C I H P L G N F S F Q S K C A F N C S E G R E L L G T A E
hHR E P T C Q V I Q C E P L S A P D L G I M N C S H P L A S F S F T S A C T

T H K M KF K VVIL K
1 10 20 30
XTYHYSEKPMNWENARKFXKQNYTDLVAIQNKXXIEYL

A A C A C
5' GAG AAG CCC ATG AAT TGG GAG AAT GC 3'

PROTEIN MOTIFS IN THE LYMPHOCYTE HOMING RECEPTOR

LYMPHOCYTE HOMING RECEPTORS

This invention was made with Government support under NIH grant No. GM23547. The Government has certain rights in this invention.

This is a divisional of co-pending application Ser. No. 07/315,015 filed on Feb. 23, 1989, now U.S. Pat. No. 5,098,833.

BACKGROUND OF THE INVENTION

This invention relates to novel lymphocyte homing receptors, to methods for making these homing receptors, and to nucleic acids encoding these receptors.

Lymphocytes are mediators of normal tissue inflammation as well as pathologic tissue damage such as occurs in rheumatoid arthritis and other autoimmune diseases. In order to fully exploit the antigenic repertoire of the immune system, vertebrates have evolved a mechanism for distributing lymphocytes with diverse antigenic specificities to spatially distinct regions of the organism (Butcher, E. C., *Curr. Top. Micro. Immunol.* 128, 85 (1986); Gallatin, W. M., et al., *Cell* 44, 673 (1986); Woodruff, J. J., et al., *Ann. Rev. Immunol.* 5, 201 (1987); Duijvestijn, A., et al., *Immunol. Today* 10, 23 (1989); Yednock, T. A., et al., *Adv. Immunol.* 44:313–78 (1989)).

This mechanism involves the continuous recirculation of the lymphocytes between the blood and the lymphoid organs. The migration of lymphocytes between the blood, where the cells have the greatest degree of mobility, and the lymphoid organs, where the lymphocytes encounter sequestered and processed antigen, is initiated by an adhesive interaction between receptors on the surface of the lymphocytes and ligands on the endothelial cells of specialized postcapillary venules, e.g., high endothelial venules (HEV) and the HEV-like vessels induced in chronically inflamed synovium.

The lymphocyte adhesion molecules have been termed homing receptors, since they allow these cells to localize in or "home" to particular secondary lymphoid organs.

Candidates for the lymphocyte homing receptor have been identified in mouse, rat and human (Gallatin, W. M., et al., *Nature* 303, 30 (1983) Rasmussen, R. A., et al., *J. Immunol.* 135, 19 (1985); Chin, Y. H., et al., *J. Immunol.* 136, 2556 (1986); Jalkanen, S., et al., *Eur. J. Immunol.* 10, 1195 (1986)). The following literature describes work which has been done in this area through the use of a monoclonal antibody, termed Mel 14, directed against a purported murine form of a lymphocyte surface protein (Gallatin, W. M., et al., supra; Mountz, J. D., et al., *J. Immunol.* 140, 2943 (1988); Lewinsohn, D. M., et al., *J. Immunol.* 138, 4313 (1987); Siegelman, M., et al., *Science* 231, 823 (1986); St. John, T., et al., *Science* 231, 845 (1986)).

Immunoprecipitation experiments have shown that this antibody recognizes a diffuse, ~90,000 dalton cell surface protein on lymphocytes (Gallatin, W. M., et al., supra) and a ~100,000 dalton protein on neutrophils (Lewinsohn, D. M., et al., supra).

A partial sequence—13 residues—for a purported lymphocyte homing receptor identified by radioactively labeled amino acid sequencing of a Mel-14 antibody-defined glycoprotein was disclosed by Siegelman et al. (Siegelman, M., et al., *Science* 231, 823 (1986)).

Lectins are a carbohydrate-binding domain found in a variety of animals, including humans as well as the acorn barnacle and the flesh fly. The concept of lectins functioning in cell adhesion is exemplified by the interaction of certain viruses and bacteria with eucaryotic host cells (Paulson, J. C., The Receptors Vol. 2 P. M. Conn, Eds. (Academic Press, N.Y., 1985), pp. 131; Sharon, N., *FEBS Lett.* 217, 145 (1987)). In eucaryotic cell-cell interactions, adhesive functions have been inferred for endogenous lectins in a variety of systems (Grabel, L., et al., *Cell* 17, 477 (1979); Fenderson, B., et al., *J. Exp. Med.* 160, 1591 (1984); Kunemund, V., *J. Cell Biol.* 106, 213 (1988); Bischoff, R., *J. Cell Biol.* 102, 2273 (1986); Crocker, P. R., et al., *J. Exp. Med.* 164, 1862 (1986); including invertebrate (Glabe, C. G., et al., *J. Cell. Biol.* 94, 123 (1982); DeAngelis, P., et al., *J. Biol. Chem.* 262, 13946 (1987)) and vertebrate fertilization (Bleil, J. D., et al., *Proc. Natl. Acad. Sci., U.S.A.* 85, 6778 (1988); Lopez, L. C., et al., *J. Cell Biol.* 101, 1501 (1985)). The use of protein-sugar interactions as a means of achieving specific cell recognition appears to be well known.

The literature suggests that a lectin may be involved in the adhesive interaction between the lymphocytes and their ligands (Rosen, S. D., et al., *Science* 228, 1005 (1985); Rosen, S. D., et al., *J. Immunol.* 142(6):1895–1902 (1989); Stoolman, L. M., et al., *J. Cell Biol* 96, 722 (1983); Stoolman, L. M., et al., *J. Cell Biol.* 99, 1535 (1984); Yednock, T. A., et al., *J. Cell Bio.* 104, 725 (1987); Stoolman, L. M., et al., *Blood* 70, 1842 (1987); A related approach by Brandley, B. K., et al., *J. Cell Biol.* 105, 991 (1987); and Yednock, T. A., et al., *J. Cell Biol.* 104, 725 (1987)).

The character of a surface glycoprotein that may be involved in human lymphocyte homing was investigated with a series of monoclonal and polyclonal antibodies generically termed Hermes. These antibodies recognized a ~90,000 dalton surface glycoprotein that was found on a large number of both immune and non-immune cell types and which, by antibody pre-clearing experiments, appeared to be related to the Mel 14 antigen. (Jalkanen, S., et al., *A.N.N. Rev. Med.*, 38, 467–476 (1987); Jalkanen, S., et al., *Blood*, 66 (3), 577–582 (1985); Jalkanen, S., et al., *J. Cell Biol.*, 105, 983–990 (1987); Jalkanen, S., et al., *Eur. J. Immunol.*, 16, 1195–1202 (1986).

Epidermal growth factor-like domains have been found on a wide range of proteins, including growth factors, cell surface receptors, developmental gene products, extracellular matrix proteins, blood clotting factors, plasminogen activators, and complement (Doolittle, R. F., et al., *CSH Symp.* 51, 447 (1986)).

The inventors have characterized the lymphocyte cell surface glycoprotein (referred to hereafter as the "LHR") which mediates the binding of lymphocytes to the endothelium of lymphoid tissue.

Accordingly, it is an object of this invention to provide nucleic acid sequences encoding the LHR.

It is another object to provide a method for expression of the LHR in recombinant cell culture.

A further object is to enable the preparation of the LHR having variant amino acid sequences or glycosylation not otherwise found in nature, as well as other derivatives of the LHR having improved properties including enhanced specific activity and enhanced plasma half-life.

SUMMARY OF THE INVENTION

The LHR of this invention is full-length, mature LHR, having the amino acid sequence described herein at FIGS. 1 and 2, and naturally occurring alleles, or predetermined amino acid sequence or derivitization or glycosylation variants thereof.

The objects of this invention have been accomplished by a method comprising providing nucleic acid encoding the LHR; transforming a host cell with the nucleic acid; culturing the host cell to allow the LHR to accumulate and recovering the LHR.

Full length cDNA clones and DNA encoding the human and the murine LHR (HuLHR and MLHR, respectively) have been identified and isolated, and moreover this DNA is readily expressed by recombinant host cells.

Analysis of the cDNA sequence reveals that the LHR is a glycoprotein which contains the following protein domains: a signal sequence, a carbohydrate binding domain, an epidermal growth factor-like (egf) domain, at least one complement binding domain repeat, a transmembrane binding domain (TMD), and a charged intracellular domain. The LHR of this invention contains at least one but not necessarily all of these domains.

Also provided are LHR having variant amino acid sequences or glycosylation not otherwise found in nature, as well as other derivatives of the LHR having improved properties including enhanced specific activity and modified plasma half-life, as well as enabling methods for the preparation of such variants.

Polynucleotide probes are provided which are capable of hybridizing under stringent conditions to the LHR gene.

BRIEF DESCRIPTION OF THE FIGURES

FIGS. 2-1 to 2-3 depict the amino acid and DNA sequence of the Murine LHR (MLHR).

FIGS. 3-1 and 3-2 show a comparison between the amino acid sequences for the mature HuLHR and MLHR.

FIG. 4A shows an SDS-polyacrylamide gel of material purified from a detergent extract of murine spleens by Mel 14 monoclonal antibody affinity chromatography. FIG. 4B shows the results of the subjection of the 90,000 dalton band of FIG. 4A to gas phase Edman degradation. The residues underlined between amino acids 7 and 15 were chosen to produce the oligonucleotide probe shown in FIG. 4C. FIG. 4C shows as 32-fold redundant 26-mer oligonucleotide probe.

FIGS. 6A-1, 6A-2, 6B, 6C-1 and 6C-2 show protein sequences which are heterologous but functionally comparable to the MLHR. Those lines labelled "MLHR" correspond to the MLHR of FIG. 2. FIG. 6A compares carbohydrate-binding domains; FIG. 6B compares epidermal growth factor domains; and FIG. 6C compares complement binding factor domains.

DETAILED DESCRIPTION

Figures 1, 3:
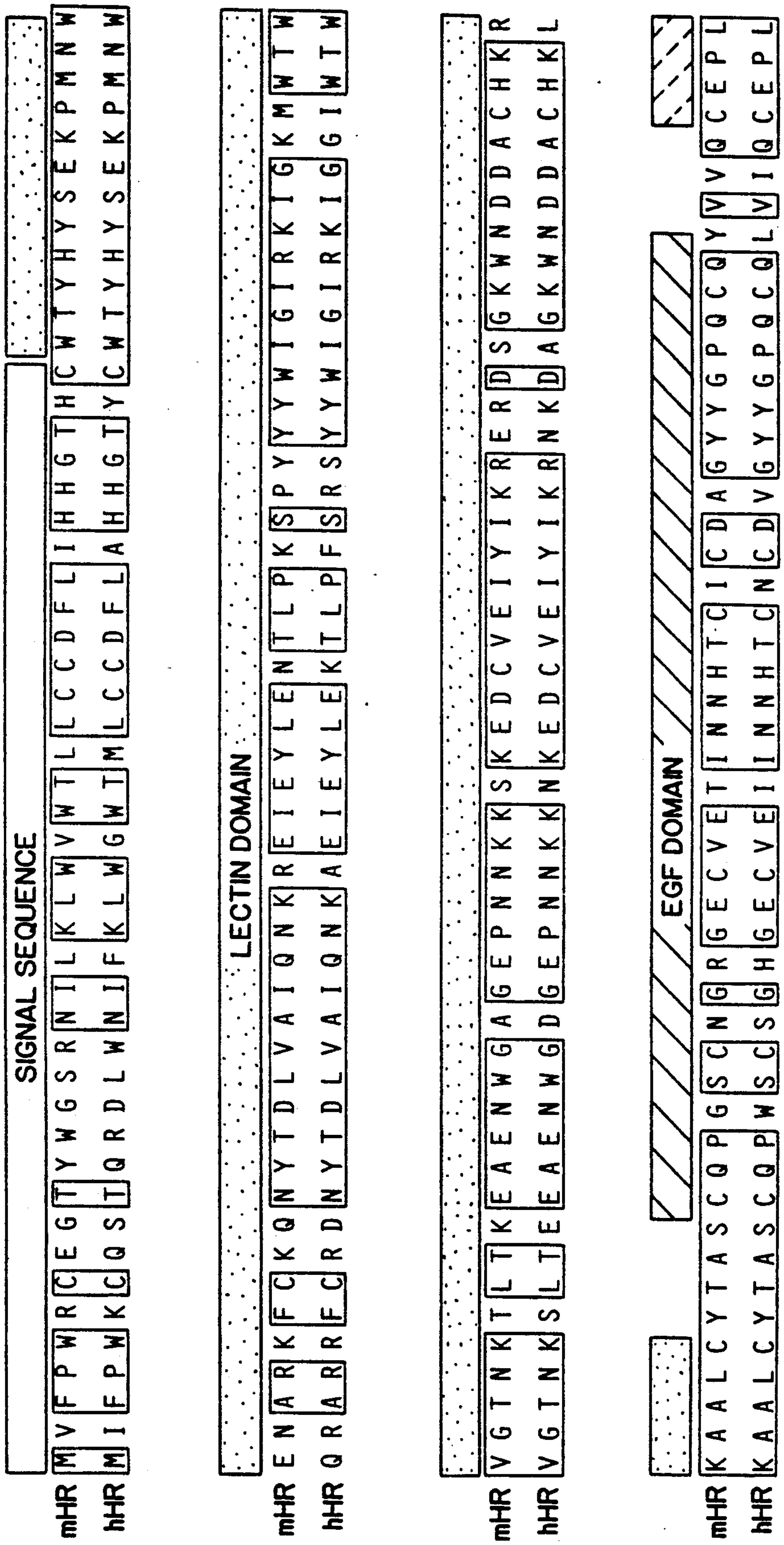
FIGS. 1-1 to 1-3 depict the amino acid and DNA sequence of the Human LHR (HuLHR).
Figures 2, 3:
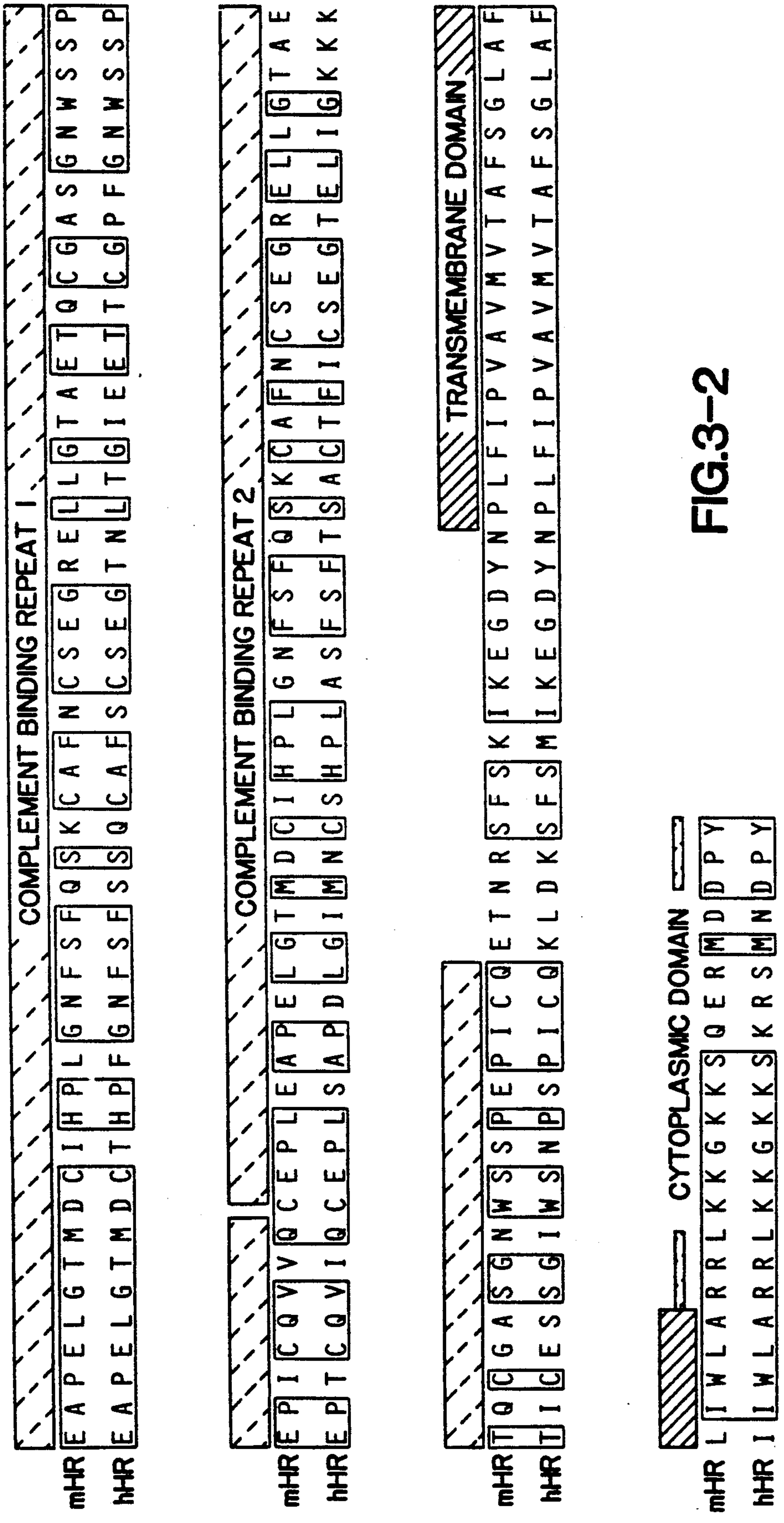

The LHR is defined as a polypeptide having a qualitative biological activity in common with the LHR of FIG. 1 or FIG. 2 and which contains a domain greater than about 70% homologous, preferably greater than about 75% homologous, and most preferably greater than about 80% homologous with a complement binding domains, the epidermal growth factor domain, or the carbohydrate binding domain of the LHR of FIG. 1 or FIG. 2.

Homologous is defined herein as the percentage of residues in the candidate sequence that are identical with the residues in the carbohydrate binding domain, the epidermal growth factor domain, or the complement binding domains in FIG. 1 or FIG. 2 after aligning the sequences and introducing gaps, if necessary, to achieve the maximum percent homology.

Included within the scope of the LHR as that term is used herein are LHRs having the amino acid sequences of the HuLHR or MLHR as set forth in FIG. 1 or 2, deglycosylated or unglycosylated derivatives of the LHR, homologous amino acid sequence variants of the sequence of FIG. 1 or 2, and homologous in-vitro-generated variants and derivatives of the LHR, which are capable of exhibiting a biological activity in common with the LHR of FIG. 1 or FIG. 2.

LHR biological activity is defined as either 1) immunological cross-reactivity with at least one epitope of the LHR, or 2) the possession of at least one adhesive, regulatory or effector function qualitatively in common with the LHR.

One example of the qualitative biological activities of the LHR is its binding to ligands on the specialized high endothelial cells of the lymphoid tissues. Also, it frequently requires a divalent cation such as calcium for ligand binding.

Immunologically cross-reactive as used herein means that the candidate polypeptide is capable of competitively inhibiting the qualitative biological activity of the LHR having this activity with polyclonal antisera raised against the known active analogue. Such antisera are prepared in conventional fashion by injecting goats or rabbits, for example, subcutaneously with the known active analogue in complete Freund's adjuvant, followed by booster intraperitoneal or subcutaneous injection in incomplete Freunds.

Structurally, as shown in FIG. 3, the LHR includes several domains which are identified as follows (within ±10 residues): a signal sequence (residues 20–32), which is followed by a carbohydrate binding domain (identified in FIG. 3 as a "lectin" domain) (residues 39–155), an epidermal growth factor (egf) domain (residues 160–193), a complement factor binding domain (residues 197–317), a transmembrane binding domain (TMD) (residues 333–355), and a cytoplasmic domain (residues 356–372). The boundary for the LHR extracellular domain generally is at, or within about 30 residues of, the N-terminus of the transmembrane domain, and is readily identified from an inspection of the LHR sequence.

Figures 1, 6A:
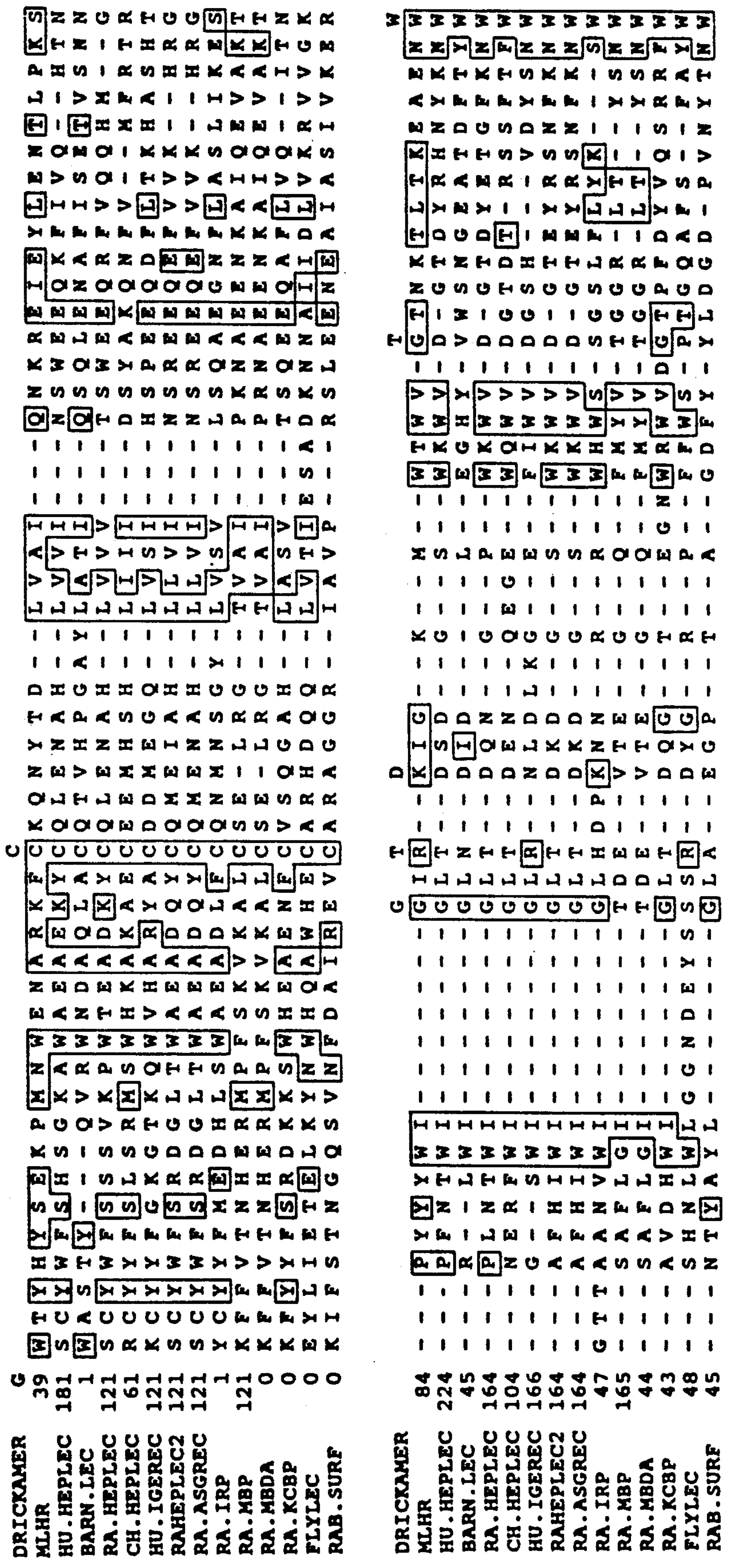
Figures 2, 6A:
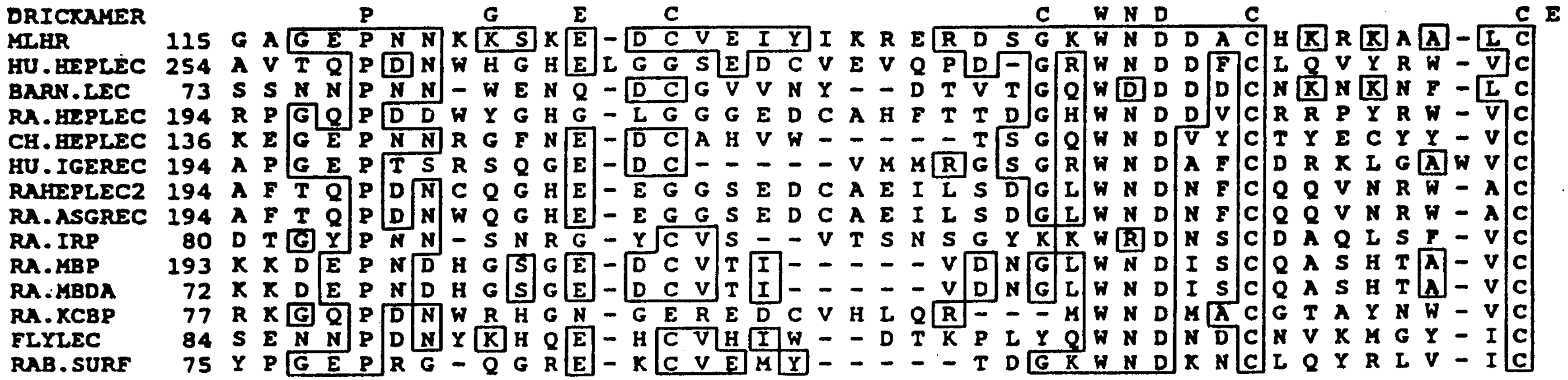
Figure 6B:
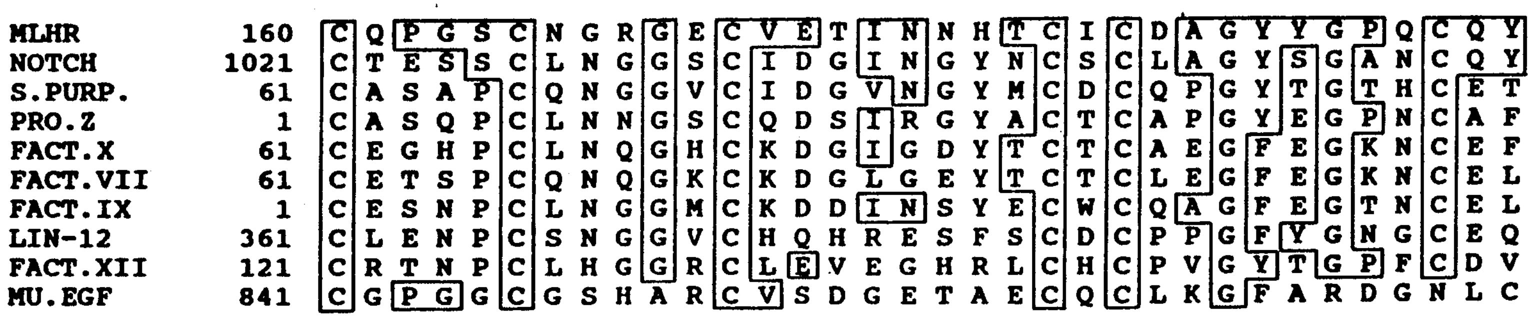
Figures 1, 6C:
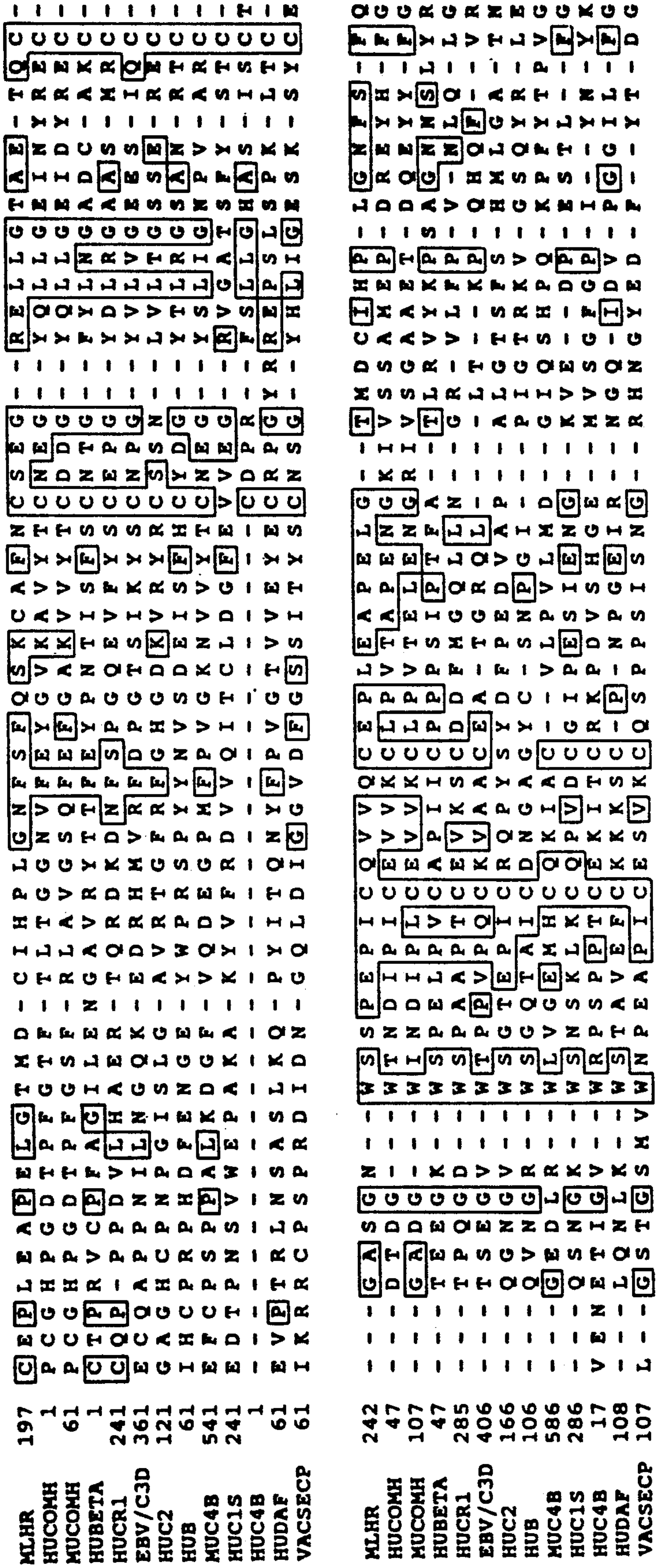
Figures 2, 6C:
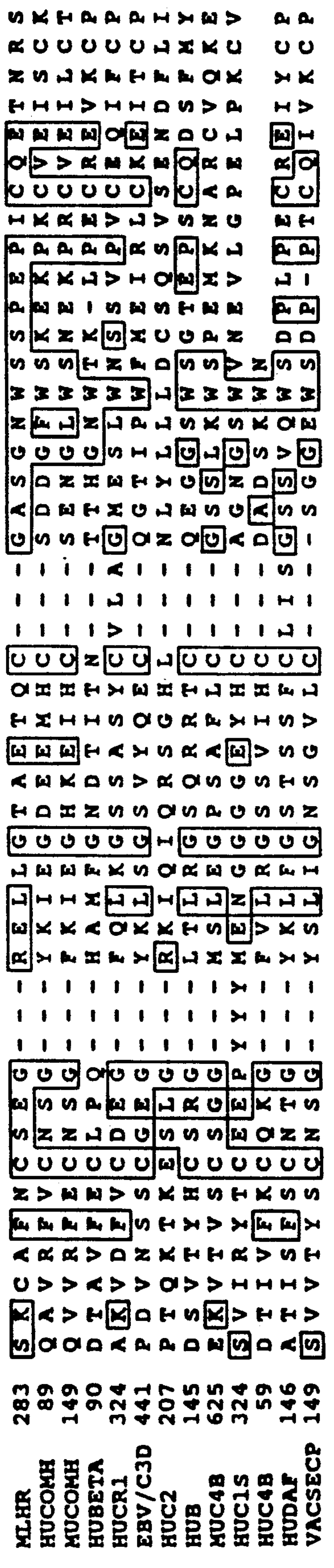

FIGS. 6A–6C show a variety of proteins having some homology to three of these domains. FIG. 6A shows carbohydrate binding domains, FIG. 6B shows epidermal growth factor domains, and FIG. 6C shows somewhat homologous complement binding domains.

A first embodiment of this invention is the HuLHR, whose nucleotide and amino acid sequence is shown in FIG. 1.

Another embodiment of the LHR of this invention is the MLHR whose nucleotide and amino acid sequence is shown in FIG. 2.

A comparison of the amino sequences of HuLHR and MLHR is presented in FIG. 3, and shows a high degree of overall sequence homology (~83%). The degrees of homology between the various domains found in the HuLHR versus the MLHR, however, are variable. For example, the degree of sequence conservation between the MLHR and the HuLHR in both the carbohydrate-binding and egf domains is approximately 83%, while the degree of conservation in the first complement binding repeat falls to 79% and only 63% in the second repeat, for an overall complement binding domain homology of ~71%. Furthermore, while the two MLHR complement binding domain repeats are identical, those in the HLHR have differences, and differ as well to the murine repeats. Interestingly, the degree of conservation between the two receptors in the transmembrane sequence and surrounding regions is virtually identical, with only one conservative hydrophobic substitution, probably within the transmembrane anchor region.

Finally, comparison of the amino acid sequence found for the HuLHR with that recently reported (Zhov, D., *B. Secd.*, submitted for publication) for the human Hermes/CD44 antigen showed a complete lack of homology between these proteins (data not shown).

This invention is particularly concerned with amino acid sequence variants of the LHR. Amino acid sequence variants of the LHR are prepared with various objectives in mind, including increasing the affinity of the LHR for its binding partner, facilitating the stability, purification and preparation of the LHR, modifying its plasma half life, improving therapeutic efficacy, and lessening the severity or occurrence of side effects during therapeutic use of the LHR.

Amino acid sequence variants of the LHR fall into one or more of three classes: Insertional, substitutional, or deletional variants. These variants ordinarily are prepared by site specific mutagenesis of nucleotides in the DNA encoding the LHR, by which DNA encoding the variant is obtained, and thereafter expressing the DNA is recombinant cell culture. However, variant LHR fragments having up to about 100–150 amino acid residues are prepared conveniently by in vitro synthesis.

The amino acid sequence variants of the LHR are predetermined variants not found in nature or naturally occurring alleles. The LHR variants typically exhibit the same qualitative biological—for example, ligand binding—activity as the naturally occurring HuLHR or MLHR analogue. However, the LHR variants and derivatives that are not capable of binding to their ligands are useful nonetheless (a) as a reagent in diagnostic assays for the LHR or antibodies to the LHR, (b) when insolubilized in accord with known methods, as agents for purifying anti-LHR antibodies from antisera or hybridoma culture supernatants, and (c)as immunogens for raising antibodies to the LHR or as immunoassay kit components (labelled, as a competitive reagent for the native LHR or unlabelled as a standard for the LHR assay) so long as at least one LHR epitope remains active.

While the site for introducing an amino acid sequence variation is predetermined, the mutation per se need not be predetermined. For example, in order to optimize the performance of a mutation at a given site, random or saturation mutagenesis (where all 20 possible residues are inserted) is conducted at the target codon and the expressed LHR variant is screened for the optimal combination of desired activities. Such screening is within the ordinary skill in the art.

Amino acid insertions usually will be on the order of about from 1 to 10 amino acid residues; substitutions are typically introduced for single residues; and deletions will range about from 1 to 30 residues. Deletions or insertions preferably are made in adjacent pairs, i.e. a deletion of 2 residues or insertion of 2 residues. It will be amply apparent from the following discussion that substitutions, deletions, insertions or any combination thereof are introduced or combined to arrive at a final construct.

Insertional amino acid sequence variants of the LHR are those in which one or more amino acid residues extraneous to the LHR are introduced into a predetermined site in the target LHR and which displace the preexisting residues.

Commonly, insertional variants are fusions of heterologous proteins or polypeptides to the amino or carboxyl terminus of the LHR. Such variants are referred to as fusions of the LHR and a polypeptide containing a sequence which is other than that which is normally found in the LHR at the inserted position. Several groups of fusions are contemplated herein.

Immunologically active LHR derivatives and fusions comprise the LHR and a polypeptide containing a non-LHR epitope, and are within the scope of this invention. The non-LHR epitope is any immunologically competent polypeptide, i.e., any polypeptide which is capable of eliciting an immune response in the animal to which the fusion is to be administered or which is capable of being bound by an antibody raised against the non-LHR polypeptide.

Typical non-LHR epitopes will be those which are borne by allergens, autoimmune epitopes, or other potent immunogens or antigens recognized by pre-existing antibodies in the fusion recipient, including bacterial polypeptides such as trpLE, betagalactosidase, viral polypeptides such as herpes gD protein, and the like.

Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into the LHR or fragment thereof by a peptide bond(s). These products therefore consist of a linear polypeptide chain containing the LHR epitope and at least one epitope foreign to the LHR. It will be understood that it is within the scope of this invention to introduce the epitopes anywhere within the LHR molecule or fragment thereof.

Such fusions are conveniently made in recombinant host cells or by the use of bifunctional cross-linking agents. The use of a cross-linking agent to fuse the LHR to the immunogenic polypeptide is not as desirable as a linear fusion because the cross-linked products are not as easily synthesized in structurally homogeneous form.

These immunogenic insertions are particularly useful when formulated into a pharmacologically acceptable carrier and administered to a subject in order to raise antibodies against the LHR, which antibodies in turn are useful in diagnostics or in purification of the LHR by immunoaffinity techniques known per se. Alternatively, in the purification of the LHR, binding partners for the fused non-LHR polypeptide, e.g. antibodies, receptors or ligands, are used to adsorb the fusion from impure admixtures, after which the fusion is eluted and, if desired, the LHR is recovered from the fusion, e.g. by enzymatic cleavage.

Other fusions, which may or may not also be immunologically active, include fusions of the mature LHR sequence with a signal sequence heterologous to the LHR, and fusions of the LHR to polypeptides having enhanced plasma half life (ordinarily >about 20 hours) such as immunoglobulin chains or fragments thereof.

Signal sequence fusions are employed in order to more expeditiously direct the secretion of the LHR. The heterologous signal replaces the native LHR signal, and when the resulting fusion is recognized, i.e. processed and cleaved by the host cell, the LHR is secreted. Signals are selected based on the intended host cell, and may include bacterial yeast, mammalian and viral sequences. The native LHR signal or the herpes gD glycoprotein signal is suitable for use in mammalian expression systems.

Plasma proteins which have enhanced plasma half-life longer than that of the transmembrane modified LHR include serum albumin, immunoglobulins, apolipoproteins, and transferrin, and desirably are fused with the LHR. Preferably, the LHR-plasma protein fusion is not significantly immunogenic in the animal in which it is used (i.e., it is homologous to the therapeutic target) and the plasma protein does not cause undesirable side effects in patients by virtue of its normal biological activity.

The LHR extracellular domain generally is fused at its C-terminus to the immunoglobulin constant region. The precise site at which the fusion is made is not critical; other sites neighboring or within the extracellular region may be selected in order to optimize the secretion or binding characteristics of the soluble LHR. The optimal site will be determined by routine experimentation. The fusion may typically take the place of either or both the transmembrane and cytoplasmic domains.

Substitutional variants are those in which at least one residue in the FIG. 1 or 2 sequence has been removed and a different residue inserted in its place. Such substitutions generally are made in accordance with the following Table 1 when it is desired to finely modulate the characteristics of the LHR.

TABLE 1

| Original Residue | Exemplary Substitutions |
|---|---|
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Novel amino acid sequences, as well as isosteric analogs (amino acid or otherwise), as included within the scope of this invention.

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in LHR properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Some deletions, insertions, and substitutions will not produce radical changes in the characteristics of the LHR molecule. However, when it is difficult to predict the exact effect of the substitution, deletion, or insertion in advance of doing so, for example when modifying the LHR carbohydrate binding domain or an immune epitope, one skilled in the art will appreciate that the effect will be evaluated by routine screening assays. For example, a variant typically is made by site specific mutagenesis of the LHR-encoding nucleic acid, expression of the variant nucleic acid in recombinant cell culture and, optionally, purification from the cell culture for example by immunoaffinity adsorption on a polyclonal anti-LHR column (in order to adsorb the variant by at least one remaining immune epitope). The activity of the cell lysate or purified LHR variant is then screened in a suitable screening assay for the desired characteristic. For example, a change in the immunological character of the LHR, such as affinity for a given antibody such as Mel-14, is measured by a competitive-type immunoassay. As more becomes known about the functions in vivo of the LHR other assays will become useful in such screening. Modifications of such protein properties as redox or thermal stability, hydrophobicity, susceptibility to proteolytic degradation, or the tendency to aggregate with carriers or into multimers are assayed by methods well known to the artisan.

Substitutional variants of the LHR also include variants where functionally homologous (having at least ~70% homology) to domains of other proteins are substituted by routine methods for one or more of the above-identified LHR domains. FIGS. 6A-6C may be used by those skilled in the art for sources for such substitutable domains. For example, the flesh fly lectin whose sequence is shown in FIG. 6A may be modified to rise to the level of at least ~70% homology with the carbohydrate binding domain of the LHR, and then substituted for that domain. Similarly, coagulation Factor X, whose sequence is shown in FIG. 6B may be modified to rise to the level of at least ~70% homology with the egf-domain of the LHR, and then substituted for that domain. Similar substitutions may desirably be made for the signal sequence, the complement binding domain, the transmembrane domain, and for the cytoplasmic domain. Only substitutions of such functionally homologous domains of other proteins which are free from all flanking regions of proteins other than the LHR are within the scope of this invention.

Another class of LHR variants are deletional variants. Deletions are characterized by the removal of one or more amino acid residues from the LHR sequence. Typically, the transmembrane and cytoplasmic domains, or only the cytoplasmic domains of the LHR are deleted. However, deletion from the LHR C-terminal to any other suitable site N-terminal to the transmembrane region which preserves the biological activity or immune cross-reactivity of the LHR is suitable. Excluded from the scope of deletional variants are the protein digestion fragments heretofore obtained in the course of elucidating amino acid sequences of the LHR, and protein fragments having less than ~70% sequence homology to any of the above-identified LHR domains.

Embodiments of this invention include DNA sequences encoding fragments of the LHR, such as the complement binding domain, the carbohydrate domain, and the epidermal growth factor domain. The complement binding domain finds usefulness in the diagnosis and treatment of complement-mediated diseases, as well as in the oligomerization of the LHR with itself or with other components on the lymphocyte surface.

Deletions of cysteine or other labile residues also may be desirable, for example in increasing the oxidative stability of the LHR. Deletion or substitutions of potential proteolysis sites, e.g. Arg Arg, is accomplished by deleting one of the basic residues or substituting one by glutaminyl or histidyl residues.

In one embodiment, the LHR is comprised of the carbohydrate binding domain in the absence of a complement binding domain and/or the egf domain. This embodiment may or may not contain either or both the transmembrane and cytoplasmic regions.

A preferred class of substitutional or deletional variants are those involving a transmembrane region of the LHR. Transmembrane regions of LHR subunits are highly hydrophobic or lipophilic domains that are the proper size to span the lipid bilayer of the cellular membrane. They are believed to anchor the LHR in the cell membrane, and allow for homo- or heteropolymeric complex formation with the LHR.

Inactivation of the transmembrane domain, typically by deletion or substitution of transmembrane domain hydroxylation residues. will facilitate recovery and formulation by reducing its cellular or membrane lipid affinity and improving its aqueous solubility. If the transmembrane and cytoplasmic domains are deleted one avoids the introduction of potentially immunogenic epitopes, either by exposure of otherwise intracellular polypeptides that might be recognized by the body as foreign or by insertion of heterologous polypeptides that are potentially immunogenic. Inactivation of the membrane binding function is accomplished by deletion of sufficient residues to produce a substantially hydrophilic hydropathy profile at this site or by substituting with heterologous residues which accomplish the same result.

A principal advantage of the transmembrane inactivated LHR is that it may be secreted into the culture medium of recombinant hosts. This variant is soluble in body fluids such as blood and does not have an appreciable affinity for cell membrane lipids, thus considerably simplifying its recovery from recombinant cell culture.

As a general proposition, all variants will not have a functional transmembrane domain and preferably will not have a functional cytoplasmic sequence.

For example, the transmembrane domain may be substituted by any amino acid sequence, e.g. a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) LHR, these variants are secreted into the culture medium of recombinant hosts.

Examples of HuLHR amino acid sequence variants are described in the table below. The residue following the residue number indicates the replacement or inserted amino acids.

| Substitutions | Deletions | Insertions |
|---|---|---|
| Arg58—Asp59: Lys—Glu | Gly96—Ile97 | 67-Glu—Ser—Ala |
| Ala71: Ser | Asn136 | 83-Gly—Thr—Thr |
| Lys78: Gln | Ser166 | 209-Asn |
| Asp116: Glu | Ser220 | 241-Val—Glu—Asn |
| Leu150: Val | Asn271 | 292-Tyr—Tyr—Tyr |
| His168: Gln | Ile296 | |
| Ile174: Leu | | |
| Asn181: Gln | | |
| Thr211: Ser | | |
| Phe214: Leu | | |
| Ser226: Thr | | |
| Phe244: Met | | |
| Thr282: Ser | | |
| Ile288: Val | | |
| Lys298—Lys299: Arg—Arg | | |
| Ile302: Leu | | |

Preferably, the variants represent conservative substitutions. It will be understood that some variants may exhibit reduced or absent biological activity. These variants nonetheless are useful as standards in immunoassays for the LHR so long as they retain at least one immune epitope of the LHR.

Glycosylation variants are included within the scope of the HuLHR. They include variants completely lacking in glycosylation (unglycosylated) and variants having at least one less glycosylated site than the native form (deglycosylated) as well as variants in which the glycosylation has been changed. Included are deglycosylated and unglycosylated amino acid sequence variants, deglycosylated and unglycosylated LHR having the native, unmodified amino acid sequence of the LHR, and other glycosylation variants. For example, substitutional or deletional mutagenesis is employed to eliminate the N- or O-linked glycosylation sites of the LHR, e.g., the asparagine residue is deleted or substituted for by another basic residue such as lysine or histidine. Alternatively, flanking residues making up the glycosylation site are substituted or deleted, even though the asparagine residues remain unchanged, in order to prevent glycosylation by eliminating the glycosylation recognition site.

Additionally, unglycosylated LHR which has the amino acid sequence of the native LHR is produced in recombinant prokaryotic cell culture because prokaryotes are incapable of introducing glycosylation into polypeptides.

Glycosylation variants are produced by selecting appropriate host cells or by in vitro methods. Yeast, for example, introduce glycosylation which varies significantly from that of mammalian systems. Similarly, mammalian cells having a different species (e.g. hamster, murine, insect, porcine, bovine or ovine) or tissue origin (e.g. lung, liver, lymphoid, mesenchymal or epidermal) than the source of the LHR are routinely screened for the ability to introduce variant glycosylation as characterized for example by elevated levels of mannose or variant ratios of mannose, fucose, sialic acid, and other sugars typically found in mammalian glycoproteins. In vitro processing of the LHR typically is accomplished by enzymatic hydrolysis, e.g. neuraminidase digestion.

Covalent modifications of the LHR molecule are included within the scope hereof. Such modifications are introduced by reacting targeted amino acid residues of the recovered protein with an organic derivatizing agent that is capable of reacting with selected side chains or terminal residues, or by harnessing mechanisms of post-translational modification that function in selected recombinant host cells. The resulting covalent derivatives are useful in programs directed at identifying residues important for biological activity, for immunoassays of the LHR or for the preparation of anti-LHR antibodies for immunoaffinity purification of the recombinant LHR. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Derivatization with bifunctional agents is useful for preparing intermolecular aggregates of the protein with immunogenic polypeptides as well as for cross-linking the protein to a water insoluble support matrix or surface for use in the assay or affinity purification of antibody. In addition, a study of intrachain cross-links will provide direct information on conformational structure. Commonly used cross-linking agents include 1,1-bis(-diazoacetyl)-2-phenylethane, glutaraldehyde, N-hydroxysuccinimide esters, for example esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane. Derivatizing agents such as methyl-3-[(p-azidophenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,080; 3,969,287; 3,691,016; 4,195,128; 4,247,642; 4,229,537; 4,055,635; and 4,330,440 are employed for protein immobilization and cross-linking.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco pp 79–86 [1983]), acetylation of the N-terminal amine and, in some instances, amidation of the C-terminal carboxyl.

Other derivatives comprise the polypeptide of this invention covalently bonded to a nonproteinaceous polymer. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyethylene esters or methoxy polyethylene glycol; polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; and heparin or heparon.

Where the polysaccharide is the native glycosylation or the glycosylation attendant on recombinant expression, the site of substitution may be located at other than a native N or O-linked glycosylation site wherein an additional or substitute N or O-linked site has been introduced into the molecule. Mixtures of such polymers may be employed, or the polymer may be homogeneous. The polymer prior to crosslinking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce crosslinking, or to purify the reaction products through gel filtration or chromatographic sieves to recover substantially homogeneous derivatives.

The molecular weight of the polymer may desirably range from about 100 to 500,000, and preferably is from about 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the polypeptide herein through a multifunctional crosslinking agent which reacts with the polymer and one or more amino acid or sugar residues of the protein. However, it is within the scope of this invention to directly crosslink the polymer by reacting a derivatized polymer with the protein, or vice versa.

The covalent crosslinking site on the polypeptide includes the N-terminal amino group and epsilon amino groups found on lysine residues, as well as other amino, imino, carboxyl, sulfhydryl, hydroxyl or other hydrophilic groups. The polymer may be covalently bonded directly to the protein without the use of a multifunctional (ordinarily bifunctional) crosslinking agent. Covalent bonding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylchloroformate or p-nitrophenylchloroformate activated PEG. Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase, (either of which produces the aldehyde derivative of the carbohydrate), followed by reaction with hydrazide or amino-derivatized polymers, in the same fashion as is described by Heitzmann et al., P.N.A.S., 71:3537-3541 (1974) or Bayer et al., Methods in Enzymology, 62:310 (1979), for the labeling of oligosaccharides with biotin or avidin. Further, other chemical or enzymatic methods which have been used heretofore to link oligosaccharides and polymers are suitable. Substituted oligosaccharides are particularly advantageous because, in general, there are fewer substitutions than amino acid sites for derivatization, and the oligosaccharide products thus will be more homogeneous. The oligosaccharide substituents also are optionally modified by enzyme digestion to remove sugars, e.g. by neuraminidase digestion, prior to polymer derivatization.

The polymer will bear a group which is directly reactive with an amino acid side chain, or the N- or C-terminus of the polypeptide herein, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

"Water soluble" in reference to the polymer conjugate means that the conjugate is soluble in physiological fluids such as blood.

The degree of substitution with such a polymer will vary depending upon the number of reactive sites on the protein, whether all or a fragment of the protein is used, whether the protein is a fusion with a heterologous protein, the molecular weight, hydrophilicity and other characteristics of the polymer, and the particular protein derivatization sites chosen. In general, the conjugate contains about from 1 to 10 polymer molecules, while any heterologous sequence may be substituted with an essentially unlimited number of polymer molecules so long as the desired activity is not significantly adversely affected. The optimal degree of crosslinking is easily determined by an experimental matrix in which the time, temperature and other reaction conditions are varied to change the degree of substitution, after which the ability of the conjugates to function in the desired fashion is determined.

The polymer, e.g. PEG, is crosslinked by a wide variety of methods known per se for the covalent modification of proteins with nonproteinaceous polymers such as PEG. Certain of these methods, however, are not preferred for the purposes herein. Cyanuric chloride chemistry leads to many side reactions, including protein cross-linking. In addition, it may be particularly likely to lead to inactivation of proteins containing sulfhydryl groups. Carbonyl diimidazole chemistry (Beauchamp et al., "Anal. Biochem." 131:25-33 [1983]) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems with purification, as both gel filtration chromatography and hydrophobic interaction chromatography are adversely effected. In addition, the high concentrations of "activated PEG" may precipitate protein, a problem that per se has been noted previously (Davis, U.S. Pat. No. 4,179,337). On the other hand, aldehyde chemistry (Royer, U.S. Pat. No. 4,002,531) is more efficient since it requires only a 40 fold molar excess of PEG and a 1-2 hr incubation. However, the manganese dioxide suggested by Royer for preparation of the PEG aldehyde is problematic "because of the pronounced tendency of PEG to form complexes with metal-based oxidizing agents" (Harris et al., "J. Polym. Sci., Polym. Chem. Ed." 22:341-352 [1984]). The use of a moffatt oxidation, utilizing DMSO and acetic anhydride, obviates this problem. In addition, the sodium borohydride suggested by Royer must be used at a high pH and has a significant tendency to reduce disulfide bonds. In contrast, sodium cyanoborohydride, which is effective at neutral pH and has very little tendency to reduce disulfide bonds is preferred.

The conjugates of this invention are separated from unreacted starting materials by gel filtration. Heterologous species of the conjugates are purified from one another in the same fashion.

The polymer also may be water insoluble, as a hydrophilic gel or a shaped article such as surgical tubing in the form of catheters or drainage conduits.

DNA encoding the LHR is synthesized by in vitro methods or is obtained readily from lymphocyte cDNA libraries. The means for synthetic creation of the DNA encoding the LHR, either by hand or with an automated apparatus, are generally known to one of ordinary skill in the art, particularly in light of the teachings contained herein. As examples of the current state of the art relating to polynucleotide synthesis, one is directed to Maniatis et al., *Molecular Cloning——A Laboratory Manual*, Cold Spring Harbor Laboratory (1984), and Horvath et al., *An Automated DNA Synthesizer Employing Deoxynucleoside 3'-Phosphoramidites*, Methods in Enzymology 154: 313-326, 1987, hereby specifically incorporated by reference.

Alternatively, to obtain DNA encoding the LHR from sources other than murine or human, since the entire DNA sequence for the preferred embodiment of the HuLHR (FIG. 1) and of the MLHR (FIG. 2) are given, one needs only to conduct hybridization screening with labelled DNA encoding either HuLHR or MLHR or fragments thereof (usually, greater than about 20, and ordinarily about 50 bp) in order to detect clones which contain homologous sequences in the cDNA libraries derived from the lymphocytes of the particular animal, followed by analyzing the clones by restriction enzyme analysis and nucleic acid sequencing to identify full-length clones. If full length clones are not present in the library, then appropriate fragments are recovered from the various clones and ligated at restriction sites common to the fragments to assemble a full-length clone. DNA encoding the LHR from other animal species is obtained by probing libraries from such species with the human or murine sequences, or by synthesizing the genes in vitro.

Included within the scope hereof are nucleic acid sequences that hybridize under stringent conditions to a fragment of the DNA sequence in FIG. 1 or FIG. 2, which fragment is greater than about 10 bp, preferably 20-50 bp, and even greater than 100 bp. Also included within the scope hereof are nucleic acid sequences that hybridize under stringent conditions to a fragment of the LHR other than the signal, or transmembrane, or cytoplasmic domains.

Included also within the scope hereof are nucleic acid probes which are capable of hybridizing under stringent conditions to the cDNA of the LHR or to the genomic gene for the LHR (including introns and 5' or 3' flanking regions extending to the adjacent genes or about 5,000 bp, whichever is greater).

Identification of the genomic DNA for the LHR is a straight-forward matter of probing a particular genomic library with the cDNA or its fragments which have been labelled with a detectable group, e.g. radiophosphorus, and recovering clone(s) containing the gene. The complete gene is pieced together by "walking" if necessary. Typically, such probes do not encode sequences with less than 70% homology to HuLHR or MLHR, and they range from about from 10 to 100 bp in length.

In general, prokaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting. Alternatively, in vitro methods of cloning, e.g. polymerase chain reaction, are suitable.

The LHR of this invention are expressed directly in recombinant cell culture as an N-terminal methionyl analogue, or as a fusion with a polypeptide heterologous to the LHR, preferably a signal sequence or other polypeptide having a specific cleavage site at the N-terminus of the LHR. For example, in constructing a prokaryotic secretory expression vector for the LHR, the native LHR signal is employed with hosts that recognize that signal. When the secretory leader is "recognized" by the host, the host signal peptidase is capable of cleaving a fusion of the leader polypeptide fused at its C-terminus to the desired mature LHR. For host prokaryotes that do not process the LHR signal, the signal is substituted by a prokaryotic signal selected for example from the group of the alkaline phosphatase, penicillinase, 1pp or heat stable enterotoxin II leaders. For yeast secretion the human LHR signal may be substituted by the yeast invertase, alpha factor or acid phosphatase leaders. In mammalian cell expression the native signal is satisfactory for mammalian LHR, although other mammalian secretory protein signals are suitable, as are viral secretory leaders, for example the herpes simplex gD signal.

The LHR may be expressed in any host cell, but preferably are synthesized in mammalian hosts. However, host cells from prokaryotes, fungi, yeast, insects and the like are also are used for expression. Exemplary prokaryotes are the strains suitable for cloning as well as *E. coli* W3110 ($F^-$, $\lambda^-$, prototrophic, ATTC No. 27325), other enterobacteriaceae such as *Serratia marcescans*, bacilli and various pseudomonads. Preferably the host cell should secrete minimal amounts of proteolytic enzymes.

Expression hosts typically are transformed with DNA encoding the LHR which has been ligated into an expression vector. Such vectors ordinarily carry a replication site (although this is not necessary where chromosomal integration will occur). Expression vectors also include marker sequences which are capable of providing phenotypic selection in transformed cells, as will be discussed further below. For example, *E. coli* is typically transformed using pBR322, a plasmid derived from an *E. coli* species (Bolivar, et al., Gene 2: 95 [1977]). pBR322 contains genes for ampicillin and tetracycline resistance and thus provides easy means for identifying transformed cells, whether for purposes of cloning or expression. Expression vectors also optimally will contain sequences which are useful for the control of transcription and translation, e.g., promoters and Shine-Dalgarno sequences (for prokaryotes) or promoters and enhancers (for mammalian cells). The promoters may be, but need not be, inducible; surprisingly, even powerful constitutive promoters such as the CMV promoter for mammalian hosts have been found to produce the LHR without host cell toxicity. While it is conceivable that expression vectors need not contain any expression control, replicative sequences or selection genes, their absence may hamper the identification of LHR transformants and the achievement of high level LHR expression.

Promoters suitable for use with prokaryotic hosts illustratively include the β-lactamase and lactose promoter systems (Chang et al., "*Nature*", 275: 615 [1978]; and Goeddel et al., "*Nature*" 281: 544 [1979]), alkaline phosphatase, the tryptophan (trp) promoter system (Goeddel "*Nucleic Acids Res.*" 8: 4057 [1980] and EPO Appln. Publ. No. 36,776) and hybrid promoters such as the tac promoter (H. de Boer et al., "*Proc. Natl. Acad.*

*Sci. USA*" 80: 21-25 [1983]). However, other functional bacterial promoters are suitable. Their nucleotide sequences are generally known, thereby enabling a skilled worker operably to ligate them to DNA encoding the LHR (Siebenlist et al., "*Cell*" 20: 269 [1980]) using linkers or adaptors to supply any required restriction sites. Promoters for use in bacterial systems also will contain a Shine-Dalgarno (S.D.) sequence operably linked to the DNA encoding the LHR.

In addition to prokaryotes, eukaryotic microbes such as yeast or filamentous fungi are satisfactory. *Saccharomyces cervisiae* is the most commonly used eukaryotic although a number of other strains are commonly available. The plasmid YRp7 is a satisfactory expression vector in yeast (Stinchcomb, et al., Nature 282: 39 [1979]; Kingsman et al., Gene 7: 141 [1979]; Tschemper et al., Gene 10: 157 [1980]). This plasmid already contains the trpl gene which provides a selection marker for a mutant strain of yeast lacking the ability to grow in tryptophan, for example ATCC no. 44076 or PEP4-1 (Jones, Genetics 85: 12 [1977]). The presence of the trpl lesion as a characteristic of the yeast host cell genome then provides an effective environment for detecting transformation by growth in the absence of tryptophan.

Suitable promoting sequences for use with yeast hosts include the promoters for 3-phosphoglycerate kinase (Hitzeman et al., "*J. Biol. Chem.*" 255: 2073 [1980]; or other glycolytic enzymes (Hess et al., "*J. Adv. Enzyme Reg.*" 7: 149 [1968]; and Holland, "*Biochemistry*"17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A.

Expression control sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3′ end of most eukaryotic genes is an AATAAA sequence which may be the signal for addition of the poly A tail to the 3′ end of the coding sequence. All of these sequences are inserted into mammalian expression vectors.

Suitable promoters for controlling transcription from vectors in mammalian host cells are readily obtained from various sources, for example, the genomes of viruses such as polyoma virus, SV40, adenovirus, MMV (steroid inducible), retroviruses (e.g. the LTR of HIV), hepatitis-B virus and most preferably cytomegalovirus, or from heterologous mammalian promoters, e.g. the beta actin promoter. The early and late promoters of SV40 are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment. Greenaway, P. J. et al., Gene 18: 355-360 (1982).

Transcription of a DNA encoding the LHR by higher eukaryotes is increased by inserting an enhancer sequence into the vector. Enhancers are cis-acting elements of DNA, usually about from 10-300 bp, that act on a promoter to increase its transcription. Enhancers are relatively orientation and position independent having been found 5′ (Laimins, L. et al., PNAS 78: 993 [1981]) and 3′ (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding the LHR. The 3′ untranslated regions also include transcription termination sites.

Expression vectors may contain a selection gene, also termed a selectable marker. Examples of suitable selectable markers for mammalian cells are dihydrofolate reductase (DHFR), thymidine kinase (TK) or neomycin. When such selectable markers are successfully transferred into a mammalian host cell, the transformed mammalian host cell is able to survive if placed under selective pressure. There are two widely used distinct categories of selective regimes. The first category is based on a cell's metabolism and the use of a mutant cell line which lacks the ability to grow independent of a supplemented media. Two examples are CHO DHFR− cells and mouse LTK− cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category of selective regimes is dominant selection which refers to a selection scheme used in any cell type and does not require the use of a mutant cell line. These schemes typically use a drug to arrest growth of a host cell. Those cells which are successfully transformed with a heterologous gene express a protein conferring drug resistance and thus survive the selection regimen. Examples of such dominant selection use the drugs neomycin (Southern et al., J. Molec. Appl. Genet. 1: 327 (1982)), mycophenolic acid (Mulligan et al., Science 209: 1422 (1980)) or hygromycin (Sugden et al., Mol. Cell. Biol. 5: 410–413 (1985)). The three examples given above employ bacterial genes under eukaryotic control to convey resistance to the appropriate drug G418 or neomycin (geneticin), xgpt (mycophenolic acid) or hygromycin, respectively.

Suitable eukaryotic host cells for expressing the LHR include monkey kidney CV1 line transformed by SV40 (COS-7, ATCC CRL 1651); human embryonic kidney line (293 or 293 cells subcloned for growth in suspension culture, Graham, F. L. et al., J. Gen Virol. 36: 59 [1977]); baby hamster kidney cells (BHK, ATCC CCL 10); chinese hamster ovary-cells-DHFR (CHO; Urlaub and Chasin, PNAS (USA) 77: 4216, [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J. P. et al., Annals N.Y. Acad. Sci. 383: 44–68 [1982]).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform *E. coli* K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9: 309 (1981) or by the method of Maxam et al., Methods in Enzymology 65: 499 (1980).

Host cells are transformed with the expression vectors of this invention and cultured in conventional nutrient media modified as appropriate for inducing promoters, selecting transformants or amplifying the LHR gene. The culture conditions, such as temperature, pH and the like, are those previously used with the host cell selected for expression, and will be apparent to the ordinarily skilled artisan.

The host cells referred to in this disclosure encompass cells in in vitro culture as well as cells which are within a host animal.

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., Virology 52: 456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., Proc. Natl. Acad. Sci. (USA), 69: 2110 (1972).

"Transfection" refers to the introduction of DNA into a host cell whether or not any coding sequences are ultimately expressed. Numerous methods of transfection are known to the ordinarily skilled artisan, for example, $CaPO_4$ and electroporation. Transformation of the host cell is the indicia of successful transfection.

The LHR is recovered and purified from recombinant cell cultures by known methods, including ammonium sulfate or ethanol precipitation, acid extraction, anion or cation exchange chromatography, phosphocellulose chromatography, immunoaffinity chromatography, hydroxyapatite chromatography and lectin chromatography. Other known purification methods within the scope of this invention utilize immobilized carbohydrates, epidermal growth factor, or complement domains. Moreover, reverse-phase HPLC and chromatography using anti-LHR antibodies are useful for the purification of the LHR. Desirably, low concentrations (approximately 1–5 mM) of calcium ion may be present during purification. The LHR may preferably be purified in the presence of a protease inhibitor such as PMSF.

The LHR is employed therapeutically to compete with the normal binding of lymphocytes to lymphoid tissue. The LHR is therefore particularly useful for organ or graft rejection, and for the treatment of patients with inflammations, such as are for example due to rheumatoid arthritis or other autoimmune diseases. The LHR also finds application in the control of lymphoma metastasis. Finally, the LHR is useful in treating conditions in which there is an accumulation of lymphocytes.

The LHR, and the LHR variants and derivatives are also useful as reagents in diagnostic assays for the LHR, antibodies to the LHR, or competitive inhibitors of LHR biological activity. When insolubilized in accord with known methods, they are useful as agents for purifying anti-LHR antibodies from antisera or hybridoma culture supernatants. The LHR which may or may not have binding activity find use as immunogens for raising antibodies to the LHR or as immunoassay kit components (labelled, as a competitive reagent for the native LHR, or unlabelled as a standard for a LHR assay).

The LHR is placed into sterile, isotonic formulations together with required cofactors, and optionally are administered by standard means well known in the field. The formulation of the LHR is preferably liquid, and is ordinarily a physiologic salt solution containing 0.5–10 mM calcium, non-phosphate buffer at pH 6.8–7.6, or may be lyophilized powder.

It is envisioned that intravenous delivery, or delivery through catheter or other surgical tubing will be the primary route for therapeutic administration. Alternative routes include tablets and the like, commercially available nebulizers for liquid formulations, and inhalation of lyophilized or aerosolized receptors. Liquid formulations may be utilized after reconstitution from powder formulations.

The LHR may also be administered via microspheres, liposomes, other microparticulate delivery systems or sustained release formulations placed in certain tissues including blood. Suitable examples of sustained release carriers include semipermeable polymer matrices in the form of shaped articles, e.g. suppositories, or microcapsules. Implantable or microcapsular sustained release matrices include polylactides (U.S. Pat. No. 3,773,919, EP 58,481) copolymers of L-glutamic acid and gamma ethyl-L-glutamate (U. Sidman et al., 1985, Biopolymers 22(1): 547–556), poly (2-hydroxyethyl-methacrylate) or ethylene vinyl acetate (R. Langer et al., 1981, J. Biomed. Mater. Res. 15: 167–277 and R. Langer, 1982, Chem. Tech. 12: 98–105). Liposomes containing the LHR are prepared by well-known methods: DE 3,218,121A; Epstein et al. 1985, Proc. Natl. Acad. Sci. USA, 82:3688–3692; Hwang et al., 1980, Proc. Natl. Acad. Sci. USA, 77:4030–4034; EP 52322A; EP 36676A; EP 88046A; EP 143949A; EP 142541A; Japanese patent application 83-11808; U.S. Pat. Nos. 4,485,045 and 4,544,545; and UP 102,342A. Ordinarily the liposomes are of the small (about 200–800 Angstroms) unilamelar type in which the lipid content is greater than about 30 mol. % cholesterol, the selected proportion being adjusted for the optimal rate of the LHR leakage.

Sustained release LHR preparations are implanted or injected into proximity to the site of inflammation or therapy, for example adjacent to arthritic joints or peripheral lymph nodes.

The dose of the LHR administered will be dependent upon the properties of the LHR employed, e.g. its activity and biological half-life, the concentration of the LHR in the formulation, the administration route for the LHR, the site and rate of dosage, the clinical tolerance of the patient involved, the pathological condition afflicting the patient and the like, as is well within the skill of the physician.

LHR may also be administered along with other pharmacologic agents used to treat the conditions listed above, such as antibiotics, anti-inflammatory agents, and anti-tumor agents. It may also be useful to administer the LHR along with other therapeutic proteins such as gamma-interferon and other immunomodulators.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

In particular, it is preferred that these plasmids have some or all of the following characteristics: (1) possess a minimal number of host-organism sequences; (2) be stable in the desired host; (3) be capable of being present in a high copy number in the desired host; (4) possess a regulatable promoter; and (5) have at least one DNA sequence coding for a selectable trait present on a portion of the plasmid separate from that where the novel DNA sequence will be inserted. Alteration of plasmids to meet the above criteria are easily performed by those of ordinary skill in the art in light of the available literature and the teachings herein. It is to be understood that additional cloning vectors may now exist or will be discovered which have the above-identified properties and are therefore suitable for use in the present invention and these vectors are also contemplated as being within the scope of this invention.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8: 4057 (1980).

"Dephosphorylation" refers to the removal of the terminal 5′ phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional. Maniatis, T. et al., *Molecular Cloning* pp. 133–134 (1982). Reactions using BAP are carried out in 50 mM Tris at 68° C. to suppress the activity of any exonucleases which are present in the enzyme preparations. Reactions are run for 1 hour. Following the reaction the DNA fragment is gel purified.

"Oligonucleotides" refers to either a single stranded polydeoxynucleotide or two complementary polydeoxynucleotide strands which may be chemically synthesized. Such synthetic oligonucleotides have no 5′ phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T. et al., *Id.*, p. 146). Unless otherwise provided, ligation is accomplished using known buffers and conditions with 10 units of T4 DNA ligase ("ligase") per 0.5 μg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15μg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 μM of each of the four deoxynucleoside triphosphates. The incubation generally is terminated after 30 min. phenol and chloroform extraction and ethanol precipitation.

It is presently believed that the three-dimensional structure of the compositions of the present invention is important to their functioning as described herein. Therefore, all related structural analogs which mimic the active structure of those formed by the compositions claimed herein are specifically included within the scope of the present invention.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention. All literature citations herein are expressly incorporated by reference.

EXAMPLES

Throughout these examples, all references to the "Mel 14" monoclonal antibody or to "Mel 14" refer to a monoclonal antibody directed against a purported murine form of a lymphocyte surface protein, as described by Gallatin, et al., supra, Nature 303, 30 (1983), specifically incorporated by reference. The use of Mel 14 is no longer needed to practice this invention, however, due to the provision herein of full sequences for the DNA and amino acids of the LHR.

EXAMPLE 1

Purification and Cloning of MLHR

Isolation of a cDNA Clone Encoding the MLHR

MLHR was isolated from detergent-treated mouse spleens by immunoaffinity chromatography using the Mel 14 monoclonal antibody.

In a typical preparation, 300 spleens from ICR female mice (16 weeks old) were minced and then homogenized with a Potter-Elvehjem tissue grinder in 180 ml of 2% Triton X-100 in Dulbecco's PBS containing 1 mM PMSF and 1% aprotinin. Lysis was continued for 30 minutes on a shaker at 4° C. The lysate was centrifuged successively at 2,000×G for 5 minutes and at 40,000×G for 30 minutes.

The supernatant was filtered through Nitex screen and then precleared by adsorption with rat serum coupled to cyanogen bromide-activated Sepharose 4B (10 ml of packed gel). The rat serum was diluted 1:10 for coupling with conjugation carried out according to the manufacturer's instructions. The flow through was applied to a 3 ml column of MEL-14 antibody coupled at 0.5 mg per ml to Sepharose 4B. All column buffers contained sodium azide at 0.02%.

The column was washed with 25 ml of 2% Triton X-100 in PBS followed by 25 ml of 10 mM CHAPS in the same buffer. Antigen was released by addition of 10 ml of 10 mM CHAPS in 100 mM glycine, 200 mM, NaCl, pH 3 and neutralized by collection into 1 ml of 1M TRIS HCl, pH 7.6. After the column was washed with 20 mM triethylamine, 200 mM NaCl, pH 11 and re-equilibrated in 10 mM CHAPS in PBS, the neutralized antigen, diluted into 100 ml of the column buffer, was re-applied and the wash and release steps were repeated.

The purified protein was concentrated in a Centricon 30 (Amicon, Inc.) and analyzed by SDS-PAGE (7.5% acrylamide) with the use of silver staining for visualization. A typical purification yielded 30–40 μg of antigen per 300 mice based upon comparisons with orosomucoid standards.

Figures 4A, 4B, 4C:
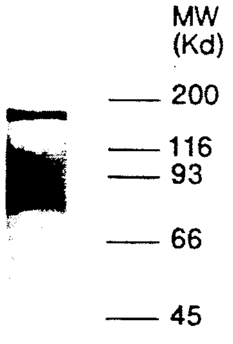
FIGS. 4A-4C show the isolation and N-terminal sequencing of the MLHR.

As can be seen in FIG. 4A, a polyacrylamide gel of the purified material showed a diffuse band migrating at approximately 90,000 daltons, and a higher molecular weight protein at around 180,000 daltons. The ratio of the 90,000 dalton to the 180,000 dalton component was 10:1 or greater in all of a large series of preparations. The material was visualized by silver staining of a 10% polyacrylamide gel.

Gas phase Edman degradation of the 90,000 dalton band resulted in the identification of a single N-terminal sequence (FIG. 4B), including the very N-terminal amino acid. 38 N-terminal amino acids were identified, with four gaps (X) at positions 1, 19, 33, and 34. The asparagine (N) at position 22 was inferred from the absence of an amino acid signal at this position combined with the following tyrosine (Y) and threonine (T) residues, resulting in an N-linked glycosylation site consensus sequence (NXT/S).

The 13-sequence residue shown in FIG. 4B above the 38 residue long N-terminus is that previously deduced by Siegelman et al., supra, using radioactively-labelled amino acid sequencing, which shows a high degree of homology (11 of 13 residues) with the sequence of the LHR determined here.

No ubiquitin sequence was obtained in any of the three sequencing runs that were done with two separate MLHR preparations. Conceivably, this modification was absent in the mouse splenocytes or the N-terminus of the ubiquitin is blocked to Edman degradation in the LHR from this source.

The amino acid sequences of FIG. 2 were compared with known sequences in the Dayhoff protein data base, through use of the algorithm of Lipman, D. et al., Science 227, 1435–1441 (1981).

The residues in FIG. 4B which are underlined between amino acids 7 and 15 were chosen to produce the oligonucleotide probe shown in FIG. 4C. A 32-fold redundant 26-mer oligonucleotide probe was designed from these residues and synthesized on an Applied Biosystems oligonucleotide synthesizer. All of the possible codon redundancies were included in this probe, with the exception of the proline at position 9, where the codon CCC was chosen based upon mammalian codon usage rules.

Screening of a murine spleen cDNA library obtained from dissected mouse spleens with this probe resulted in the isolation of a single hybridizing cDNA clone. Procedurally, 600,000 plaques from an oligo dT-primed lambda gt 10 murine spleen cDNA library produced from mRNA isolated from murine splenocytes with 5 μg/ml Concanavalin A for 6 hours were plated at 50,000 phage per plate (12 plates) and hybridized with the $P^{32}$ labeled 32-fold redundant 26-mer oligonucleotide probe shown in FIG. 4C, in 20% formamide, 5XSSC (150 mM NaCl, 15 mM trisodium citrate), 50 mM sodium phosphate (pH7.6), 5× Denhardts solution, 10% dextran sulfate, and 20 micrograms/ml denatured, sheared salmon sperm DNA overnight at 42° C. These parameters are referred to herein as "stringent conditions". The filters were washed in 1× SSC, 0.1% SDS at 42° C. for 2× 30 minutes and autoradiographed at −70° C. overnight. A single duplicate positive clone was rescreened, the EcoR1insert was isolated and inserted into M13 or PUC 118/119 vectors and the nucleotide sequence determined from single stranded templates using sequence-specific primers.

FIG. 2 shows the complete DNA sequence of the 2.2 kilobase EcoR1 insert contained in this bacteriophage. The longest open reading frame begins with a methionine codon at position 106–108. A Kozak box homology is found surrounding this methionine codon, suggesting that this codon probably functions in initiating protein translation. A protein sequence containing 373 amino acids of approximately 42,200 daltons molecular weight is encoded within this open reading frame. The translated protein shows a sequence from residues 40 to 76 that corresponds exactly with the N-terminal amino acid sequence determined from the isolated MLHR.

This result suggests that the mature N-terminus of the MLHR begins with the tryptophan residue at position 39. However, it is believed that some proteolytic processing of the actual N-terminus of the LHR may have occurred during the isolation of the protein.

A hydrophobicity profile of the protein reveals an N-terminally located hydrophobic domain that could function as a signal sequence for insertion into the lumen of the endoplasmic reticulum. The deduced sequence for positions 39 to 333 is predominantly hydrophilic followed by a 22 residue hydrophobic domain, which is characteristic of a stop transfer or membrane anchoring domain.

The putative intracellular region at the very C-terminus of the protein is quite short, only 17 residues in length. On the immediate C-terminal side of the predicted membrane-spanning domain are several basic amino acids, a feature typical of junctions between membrane anchors and cytoplasmic domains of cell surface receptors, Yarden et al., Nature. A single serine residue, potentially a site for phosphorylation, is present within the putative cytoplasmic domain.

The protein contains ten potential N-linked glycosylation sites, all of which are within the projected extracellular domain. The absence of asparagine at position 60 (residue 22 of the mature protein) in the peptide sequencing analysis confirms glycosylation at this site and establishes the extracellular orientation of this region. The coding region contains a total of 25 cysteine residues, although 4 of these cysteine residues are located within the putative leader sequence.

Protein Motifs Within the MLHR

As shown in FIG. 6, comparison of the deduced MLHR amino acid sequence to other proteins in the Dayhoff protein sequence databank by using the fastp program (Lipman, D., and Pearson, W., Science 227, 1435–1441, 1985) revealed a number of interesting sequence homologies.

Proteins with the highest sequence homology scores are shown with boxes surrounding the regions of greatest sequence homology. The numbers at the beginning of the sequences show the position within the proteins where these homologous sequences are located.

FIG. 6A shows that the N-terminal motif of the LHR (residues 39 to 155) has certain carbohydrate binding protein homologies, as listed (the percentage of homology of these sequences to the MuLHR are given in parentheses, and the references indicated are provided after the Examples): Drickamer; the amino acid residues found by Drickamer et al. (1), MLHR; the MLHR sequence, Hu.HepLec (27.8%); human hepatic lectin (2), Barn.Lec (25%); acorn barnacle lectin (3), Ra. HepLec (23.5%); rat hepatic lectin (4), Ch.HepLec (27.5%); chicken hepatic lectin (5), Hu.IgERec (28.6%); human IgE receptor (6), RaHepLec2 (22.6%); rat hepatic lectin 2 (7), Ra.ASGRec (22.6%); rat asialoglycoprotein receptor (8), Ra.IRP (25.6%); rat islet regenerating protein (9), Ra.MBP (26.1%); rat mannose binding protein (10 ), Ra.MBDA (26.1%); rat mannose binding protein precursor A (11), Ra.KCBP (27%); rat Kuppfer cell binding protein (12), FlyLec (23.1%); flesh fly (Sarcophaga) lectin (13), and Rab.Surf (20.9%); rabbit lung surfactant (14).

As can be seen, FIG. 6A shows that the most N-terminally localized motif of the LHR shows a high degree of homology with a number of calcium-dependent animal lectins, i.e., C-type lectins (1). These include but are not limited to, various hepatic sugar binding proteins from chicken, rat, and human, soluble mannose-binding lectins, a lectin from Kupffer cells, the asialoglycoprotein receptor, a cartilage proteoglycan core protein, pulmonary surfactant apoproteins, and two invertebrate lectins from the flesh fly and acorn barnacle. Although the complement of "invariant" amino acids initially recognized by Drickamer and colleagues, supra, as common to C-type animal lectins are not completely conserved in the carbohydrate binding domain of the MLHR, the degree of homology at these residues and at other positions is apparent. The known lectins belonging to the C-type family exhibit a range of sugar-binding specificities including oligosaccharides with terminal galactose, N-acetylglucosamine, and mannose (1).

Interestingly, the lectin domains of all of these proteins except the acorn barnacle lectin and the flesh fly lectin are located in their respective carboxy-termini, suggesting that this MLHR domain may be contained in an exon that can be shuffled to different proteins for different functions.

The fact that there are many residues that are found to be invariant in all of these carbohydrate binding proteins, strongly suggests that this region functions as a carbohydrate binding domain in the MLHR and apparently explains the observed ability of lymphocytes to bind to the specialized endothelium of lymphoid tissue in a sugar- and calcium-dependent manner. It is believed that the carbohydrate binding domain of the LHR alone, without any flanking LHR regions, is desirably used in the practice of this invention.

The next motif (residues 160–193) that is found almost immediately after the completion of the carbohydrate binding domain shows a high degree of homology to the epidermal growth factor (egf) family. FIG. 6B shows epidermal growth factor (egf) homologies: MLHR; the MLHR sequence, Notch (38.5%); the Drosophila melanogaster notch locus (15), S. purp (31.7%); Strongylocentrotur purpuratus egf-like protein (16), Pro.Z (34.1%); bovine protein Z (17), Fact.X (34.2%); coagulation factor X (18), Fact.VII (27.3%); coagulation factor VII (19), Fact.IX (33.3%); coagulation factor IX (20), Lin-12 (32.1%); Caenorhabditis elegans Lin-12 locus (21), Fact. XII (26%); coagulation factor XII (22), and Mu.egf (30%); murine egf (23).

As can be seen in FIG. 6B, the greatest degree of homology in this region of the MLHR is found with the Drosophila neurogenic locus, notch, although there is also significant homology to a number of other members of this large family. The variable location of this domain among the members of this family suggests that this region may be contained within a genomic segment that can be shuffled between different proteins for different functions.

In addition to 6 cysteine residues, virtually all members of this family share three glycine residues. The conservation of cysteine and glycine residues is consistent with the possibility of a structural role for this region in the LHR. It is believed that this domain may place the N-terminally localized carbohydrate binding region in an appropriate orientation for ligand interaction. It is further believed that this domain may serve to strengthen the interaction between the lymphocyte and endothelium by binding to an egf-receptor homologue on the endothelium surface.

The final protein motif in the extracellular region of the MLHR is encoded from amino acids 197 to 328. This region of the glycoprotein contains two direct repeats of a 62 residue sequence that contains an amino acid motif that bears a high degree of homology to a number of complement factor binding proteins (FIG. 6C).

FIG. 6C shows complement binding protein homologies: MLHR; MLHR sequence, HuComH (31.9%); human complement protein H precursor (24), MuComH (28.9%); murine complement protein H precursor (25), HuBeta (25.6%); human beta-2-glycoprotein I (26), HuCR1 (29.9%); human CR1 (27), EBV/3d (25%)6; human Epstein-Barr virus/C3d receptor (28), HuC2 (27.1%); human complement C2 precursor (29), HuB (23.1%); human complement factor B (30), MuC4b (22%); murine C4b-binding precursor (31), HuCls (29.2%); human Cls zymogen (32), HuC4b (26.1%); human C4b binding protein (33), HuDAF (27.1%); human decay accelerating factor (34), VacSecP (26.2%); vaccinia virus secretory peptide (35).

These proteins, which encode a wide range of multiples of this repeated domain, include, among others, the human and murine complement H precursors, the human beta 2 glycoprotein, the Epstein Barr virus/C3d receptor, the human C4b binding protein, the decay accelerating factor, and the vaccinia virus secretory polypeptide.

FIG. 7C shows the homologies between the two direct repeats in the MLHR and the direct repeats found in proteins contained within the complement binding family. Many of the amino acids that are conserved in this class of complement binding proteins, including a number of conserved cysteine residues, are also found in the 2 repeats in this region of the MLHR.

Interestingly, the two repeats contained within the MLHR are not only exact duplications of each other at the amino acid level, they also show exact homology at the nucleotide sequence level (nucleotide residues 685–865 and 866–1056). While it is possible that this result is due to a cloning artifact, a duplicated region has been found in a number of other clones isolated from a separate cDNA library produced from the MLHR expressing cell line, 38C13 (available from Stanford University, Palo Alto, Calif., U.S.A.), as well as in a human homologue of the MLHR (discussed, infra.). Furthermore, a number of other genes, most notably the Lp(a) gene, show an even higher degree of intragenic repeat sequence conservation of this domain. These results suggest that the MLHR, like other members of the complement binding family, contains multiple repeats of this binding domain.

Figure 7:
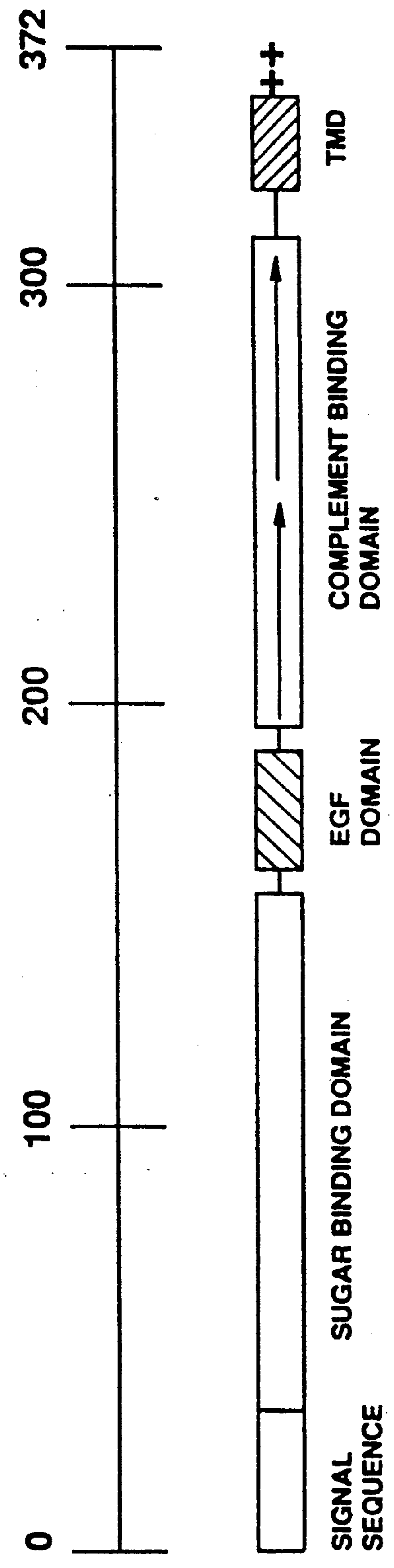
FIG. 7 is a schematic of protein domains found in the LHR, including the signal sequence, carbohydrate binding domain, epidermal growth factor (egf) domain, two complement binding domain repeats (arrows), transmembrane binding domain (TMD), and charged intracellular domain.

In conclusion, it appears that the extracellular region of the MLHR contains three separate protein motifs that have been joined together to serve a new function or functions. A summary of the protein motifs contained within this glycoprotein is shown in FIG. 7.

EXAMPLE 2

Cloning of HuLHR

Generally as described in the previous example, the 2.2 kb EcoR1 insert of the murine Mel 14antigen cDNA clone described above was isolated, labeled to high specific activity by randomly primed DNA polymerase synthesis with $P^{32}$ triphosphates, and used to screen 600,000 clones from an oligo dT primed lambda gt10 cDNA library derived from human peripheral blood lymphocyte mRNA obtained from primary cells. The filters were hybridized overnight at 42° C. in 40% formamide, 5× SSC (1× SSC is 30 mM NaCl, 3 mM trisodium citrate), 50 mM sodium phosphate (pH6.8), 10% dextran sulfate, 5× Denhardt's solution and 20 micrograms/ml sheared, boiled salmon sperm DNA. They were washed 2×40 minutes in 0.2× SSC, 0.1% sodium dodecyl sulfate at 55° C. 12 clones (approximately 1 positive per plate of 50,000 phage) were picked, and the largest EcoR1 insert (~2.2 kilobases) was isolated and the DNA sequence was determined by didoxynucleotide sequencing in the bacteriophage m13 using sequence-specific primers.

This ~2.2 kb clone encoded an open reading frame of 372 amino acids with a molecular weight of approximately 42,200 daltons that began with a methionine which was preceded by a Kozak box homology. The encoded protein contained 26 cysteine residues and 8 potential N-linked glycosylation sites. A highly hydrophobic region at the N-terminus of the protein (residues 20–33) was a potential signal sequence, while another highly hydrophobic C-terminally located region of 22 amino acids in length (residues 335–357) was a potential stop transfer or membrane anchoring domain. This C-terminal hydrophobic region was followed by a charged, presumably cytoplasmic, region.

Comparison of the nucleotide sequence of this human clone with that previously found for the MLHR showed a high degree of overall DNA sequence homology (~83%). The relative degrees of amino acid sequence conservation between the MLHR and the HuLHR in each of the LHR domains are: carbohydrate binding domain—83%; egf-like domain—82%; complement binding repeat 1—79%; complement binding repeat 2—63%; overall complement binding domain—71%; and transmembrane domain—96%.

Comparison of the published Hermes sequence, Jalkanen, supra, with the HuLHR sequence of FIG. 1 reveals a lack of sequence homology.

EXAMPLE 3

Expression of the MLHR

In order to conclusively prove that the murine cDNA clone isolated here encoded the MLHR, the clone was inserted into an expression vector and analyzed in a transient cell transfection assay. Expression of the HuLHR was performed in a similar fashion.

The Eco R1 fragment containing the open reading frame described above (the ~2.2 kilobase EcoR1 fragment whose sequence is shown in FIG. 2) was isolated and ligated into the pRK5 vector which contains a cytomegalovirus promoter (Eaton, D., et al., Biochemistry 25, 8343–8347, 1986; U.S. Ser. No. 07/097,472). A plasmid containing the inserted cDNA in the correct orientation relative to the promoter was selected and transfected onto 293 human embryonic kidney cells using $CaPO_4$ precipitation.

After 2 days the cells were incubated with 500 microcuries each of $S^{35}$ cysteine and methionine. Lysates and supernatants were prepared as previously described (Lasky, L., et al., Cell 50, 975–985, 1987) and immunoprecipitated with Mel 14monoclonal antibody (purified by immunoaffinity chromatography) by utilizing an anti-rat IgG polyclonal antibody in a sandwich between the Mel 14 monoclonal antibody and protein A sepharose.

At the same time, the B-cell lymphoma, 38C13, a cell known to express the MLHR, were either labeled metabolically with either methionine or cysteine, for analysis of the supernatant MLHR, or the cell-surface glycoproteins were labeled with $I^{125}$ and lactoperoxidase for analysis of cell-associated LHR and analyzed by Mel 14antibody immunoprecipitation.

The resultant immunoprecipitates were analyzed on 7.5% polyacrylamide SDS gels and autoradiographed overnight at −70° C.

Figure 5:
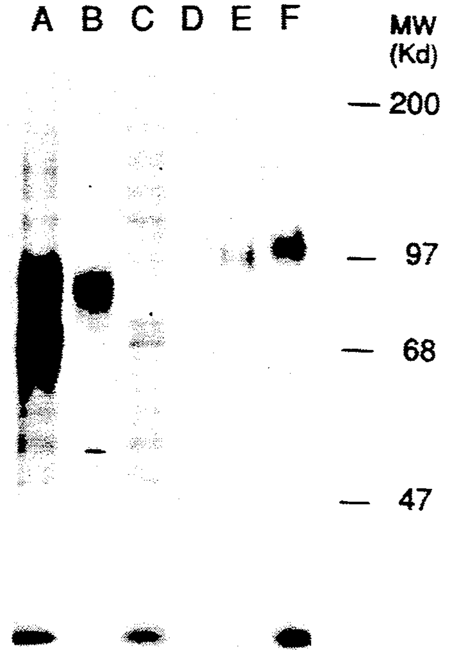
FIG. 5 shows the transient expression of the MLHR cDNA clone. Lanes A–F signify the following: —A. Lysates of 293 cells transfected with a MLHR expression plasmid immunoprecipitated with Mel 14 monoclonal antibody. —B. Supernatants of 293 cells transfected with a MLHR expression plasmid immunoprecipated with Mel 14 monoclonal antibody. —C. Lysates of 293 cells transfected with a plasmid expressing the HIV gp120 envelope glycoprotein immunoprecipitated with the Mel 14 monoclonal antibody. —D. Supernatants of 293 cells transfected with the HIV envelope expression plasmid immunoprecipitated with the Mel 14 monoclonal antibody. —E. Supernatants of 38C13 cells immunoprecipitated with the Mel 14 monoclonal antibody. —F. Lysates of 38C13 cells surface labeled with $I^{125}$ and immunoprecipitated with Mel 14 monoclonal antibody.

The results of these assays are shown in FIG. 5. In that figure, the lanes A–F signify the following:

A. Lysates of 293 cells transfected with a MLHR expression plasmid immunoprecipitated with Mel 14monoclonal antibody.

B. Supernatants of 293 cells transfected with a MLHR expression plasmid immunoprecipitated with Mel 14monoclonal antibody.

C. Lysates of 293 cells transfected with a plasmid expressing the HIV gp120 envelope glycoprotein immunoprecipitated with the Mel 14monoclonal antibody.

D. Supernatants of 293 cells transfected with the HIV envelope expression plasmid immunoprecipitated with the Mel 14 monoclonal antibody.

E. Supernatants of 38C13 cells immunoprecipitated with the Mel 14monoclonal antibody.

F. Lysates of 38C13 cells surface labeled with $I^{125}$ and immunoprecipitated with the Mel 14monoclonal antibody.

As can be seen in FIG. 5, cells transfected with this construct produce two cell-associated proteins that reacted specifically with the Mel 14antibody. The cell associated proteins migrated at approximately ~70,000 daltons and ~85,000 daltons, suggesting that the ~42,200 dalton core protein becomes glycosylated in the transfected cells. The larger band was shifted in molecular weight following sialidase treatment (data not shown), suggesting that it is a relatively mature form of the glycoprotein, whereas the lower molecular weight band was resistant to the enzyme, indicating that it may be a precursor form.

FACs analysis of transiently transfected cell lines with the Mel 14antibody showed that a portion of the LHR expressed in these cells was detectable on the cell surface (data not shown).

The higher molecular weight glycoprotein produced in the transfected cell line was found to be slightly smaller than that produced by the Peripheral Lymph Node-homing B-cell lymphoma, 38C13 (FIG. 5, lane F), a result that has been found in other transfected cell lines and may be due to cell-specific differences in glycosylation.

Interestingly, both the 38C13 cells and the transfected human cells appeared to shed a smaller molecular weight form of the MLHR into the medium (FIG. 5, lanes B and E). The nature of this shed molecule is unclear, although its reduced molecular weight suggests that it may be a cleavage product of the cell surface form resulting from proteolysis near the membrane anchor.

In conclusion, these results convincingly demonstrate that the cDNA clone that we have isolated encodes the MLHR.

REFERENCES TO THE EXAMPLES

1. Drickamer, K., *J. Biol. Chem.* 263, 9557 (1988); Drickamer, K., *Kidney Int.* 32, S167 (1987).
2. Spiess, M., et al., *Proc. Natl. Acad. Sci., U.S.A.* 82, 6465 (1985).
3. Muramoto, K., et al., *Biochem Biophys. Acta* 874, 285 (1986).
4. Leung, J., et al., *J. Biol. Chem.* 260, 12523 (1985); Holland, E., et al., *Proc. Natl. Acad. Sci., U.S.A.* 81, 7338 (1984).
5. Drickamer, K., *J. Biol. Chem.* 256, 5827 (1981).
6. Kikutani, H., et al., *Cell* 47, 657 (1986).
7. McPhaul, M., et al., *Molec. Cell. Biol.* 7, 1841 (1987).
8. Halberg, D., et al., *J. Biol. Chem.* 262, 9828 (1987).
9. Terzaono, K., et al., *J. Biol. Chem.* 263, 2111 (1988).
10. Drickamer, K., et al., *J. Biol. Chem.* 262, 2582 (1987).
11. Drickamer, K., et al., *J. Biol. Chem.* 261, 6878 (1986).
12. Hoyle, G., et al., *J. Biol. Chem.* 263, 7487 (1988).
13. Takahashi, H., et al., *J. Biol. Chem.* 260, 12228 (1985).
14. Boggaram, V., et al., *J. Biol. Chem.* 263, 2939 (1988).
15. Kidd, S., et al., *Mol. Cell. Biol.* 6, 3094 (1986).
16. Hursh, D., et al., *Science* 237, 1487 (1987).
17. Hojrup, P., et al., *FEBS Lett.* 184, 333 (1985).
18. Fung, M., et al., *Nucl. Acids Res.* 12, 4481 (1984).
19. Takeya, H. et al., *Proc. Natl. Acad. Sci., U.S.A.* 76, 4990 (1979).
20. McMullen, B., et al., *Biochem Biophys. Res. Commun.* 115, 8 (1983).
21. Greenwald, I., *Cell* 43, 583 (1985).
22. Cool, D., et al., *Biol. Chem.* 260, 13666 (1985).
23. Gray, A., et al., *Nature* 303, 722 (1983).
24. Schulz, T., et al., *Eur. J. Immunol.* 16, 1351 (1986).
25. Kristensen, T., et al., *Proc. Natl. Acad. Sci., U.S.A.* 83, 3963 (1986).
26. Lozier, J., et al., *Proc. Natl. Acad. Sci., U.S.A.* 81, 3640 (1984).
27. Bentley, D. *Biochem. J.* 239, 339 (1986).
28. Moore, M. et al., *Proc. Natl. Acad. Sci., U.S.A.,* 84, 9194 (1987).
29. Bentley, D., et al., *Proc. Natl. Acad. Sci., U.S.A.,* 81, 1212 (1984).
30. Mole, J., et al., *J. Biol. Chem.* 259, 3407 (1984).
31. DiScipio, R., et al., *J. Biol. Chem.* 263, 549 (1988).
32. Kusomoto, H., et al., *Proc. Natl. Acad. Sci., U.S.A.* 85, 7307 (1988).
33. Lintin, S., et al., *FEBS Lett.* 204, 77 (1986).
34. Caras, I., et al., *Nature* 325, 545 (1987).
35. Kotwal, G., et al., *Nature* 335, 176 (1988).

We claim:

1. A human LHR (HuLHR) comprising the carbohydrate binding domain, the epidermal growth factor domain and a complement binding domain of the amino acid sequence shown in FIG. 1 purified to show a single band on SDS-PAGE as visualized by silver stain, and having LHR biological activity.

2. The LHR of claim 1, wherein the LHR is not associated with native glycosylation.

3. The LHR of claim 1, wherein the LHR has variant glycosylation.

4. The LHR of claim 1 in a physiologically acceptable carrier.

5. The huLHR of claim 1 in which the transmembrane domain has been inactivated.

6. The huLHR of claim 1 from which the transmembrane domain has been deleted.

7. The huLHR of claim 6 from which the cytoplasmic domain has been deleted.

8. A murine LHR (MLHR) comprising the carbohydrate binding domain, the epidermal growth factor domain and a complement binding domain of the amino acid sequence shown in FIG. 2 purified to show a single band on SDS-PAGE as visualized by silver stain, and having LHR biological activity.

9. A polypeptide encoded by a DNA able to hybridize under stringent conditions to the complement of a DNA sequence encoding the carbohydrate binding domain, the epidermal growth factor domain or a complement binding domain of the LHR amino acid sequence shown in FIG. 1 or FIG. 2 purified to show a single band on SDS-PAGE as visualized by silver stain, and having LHR biological activity.

10. The LHR of claim 9 which binds to the high endothelial venules of lymphoid tissue.

11. The polypeptide of claim 9 wherein the stringent conditions are overnight incubation at 42° C. in a solution comprising: 20% formamide, 5XSSC (150 mM NaCl, 15 mM trisodium citrate), 50 mM sodium phosphate (pH 7.6), 5XDenhard's solution, 10% dextrane sulfate, and 20 μg/ml denatured, sheared salmon sperm DNA.

12. The polypeptide of claim 9 encoded by a DNA able to hybridize under stringent conditions to the complement of a DNA encoding the carbohydrate binding domain of the LHR amino acid sequence shown in FIG. 1 or FIG. 2.

13. The polypeptide of claim 9 which is devoid of a functional transmembrane domain.

14. The polypeptide of claim 9 which is devoid of a functional cytoplasmic domain.

15. Mature HuLHR having the amino acid sequence shown in FIG. 1 purified to show a single band on SDS-PAGE as visualized by silver stain.

16. Mature MLHR having the amino acid sequence shown in FIG. 2 purified to show a single band on SDS-PAGE as visualized by silver stain.

* * * * *

UNITED STATES PATENT AND TRADEMARK OFFICE

CERTIFICATE OF CORRECTION

PATENT NO. : 5,216,131
DATED : June 1, 1993
INVENTOR(S) : Lasky, Et al.

It is certified that error appears in the above-identified patent and that said Letters Patent is hereby corrected as shown below:

Title page item [73], line 2, delete "Francisco," and insert therefor --Francisco; The Regents of the University of California, Oakland, both of--

Signed and Sealed this

Twelfth Day of December, 2000

*Attest:*

Q. TODD DICKINSON

*Attesting Officer* *Director of Patents and Trademarks*